United States Patent
Garg et al.

(10) Patent No.: US 6,706,276 B2
(45) Date of Patent: Mar. 16, 2004

(54) COMPOSITIONS AND METHODS FOR TRAPPING AND INACTIVATING PATHOGENIC MICROBES AND SPERMATOZOA

(75) Inventors: Sanjay Garg, Punjab (IN); Lourens Jan Dirk Zaneveld, Chicago, IL (US); Robert Anthony Anderson, Jr., Chicago, IL (US); Donald Paul Waller, Oak Brook, IL (US)

(73) Assignee: Rush-Presbyterian-St. Luke's Medical Center, Chicago, IL (US)

( * ) Notice: Subject to any disclaimer, the term of this patent is extended or adjusted under 35 U.S.C. 154(b) by 0 days.

(21) Appl. No.: 09/800,036

(22) Filed: Mar. 6, 2001

(65) Prior Publication Data

US 2004/0009223 A1 Jan. 15, 2004

Related U.S. Application Data

(60) Provisional application No. 60/187,574, filed on Mar. 7, 2000.

(51) Int. Cl.$^7$ ............................. A61F 13/00; A61K 9/14

(52) U.S. Cl. ...................... 424/433; 424/430; 424/488; 424/464

(58) Field of Search ................................. 424/488, 433, 424/430, 464, 484, 400

(56) References Cited

U.S. PATENT DOCUMENTS

| | | |
|---|---|---|
| 4,005,220 A | 1/1977 | Esteve-Subirana |
| 5,166,173 A | 11/1992 | Hwang et al. |
| 5,196,452 A | 3/1993 | Hwang et al. |
| 5,308,612 A | 5/1994 | Lee |
| 5,312,837 A | 5/1994 | Hwang et al. |
| 5,314,904 A | 5/1994 | Egidio et al. |
| 5,441,983 A | 8/1995 | Hwang et al. |
| 5,482,053 A | 1/1996 | Kelly |
| 5,536,743 A * | 7/1996 | Borgman ................ 514/39.8 |
| 5,545,673 A | 8/1996 | Kelly |
| 5,599,551 A | 2/1997 | Kelly |
| 5,617,877 A | 4/1997 | Moench et al. |
| 5,624,675 A | 4/1997 | Kelly |
| 5,667,492 A | 9/1997 | Bologna et al. |
| 5,700,679 A | 12/1997 | Wright |
| 5,741,525 A | 4/1998 | Larsen |
| 5,840,744 A | 11/1998 | Borgman |
| 5,863,553 A * | 1/1999 | Britton et al. ............... 424/433 |
| 5,925,621 A | 7/1999 | Zaneveld et al. |
| 5,932,619 A | 8/1999 | Zaneveld et al. |
| 6,017,521 A | 1/2000 | Robinson et al. |
| 6,028,115 A | 2/2000 | Zaneveld et al. |
| 6,063,773 A | 5/2000 | Anderson et al. |
| 6,125,850 A | 10/2000 | Sokal et al. |
| 6,239,182 B1 * | 5/2001 | Zaneveld et al. ........... 514/764 |

OTHER PUBLICATIONS

Godfrey, S. E., "Heterosexual Transmission of HIV", JAMA, Apr. 8, 1992, vol. 267, No. 14.pp. 1917–1919.

Forbes, A., "Vaginal Dreams", HIV Plus, Dec. 1998, pp. 20–22.

Robinson, J. R., et al., "Vaginal and reproductive system treatments using a bioadhesive polymer", *Journal of Controlled Release*, 28 (1994) pp. 87–94.

Rogers, H. J., et al., (1954) "Synthetic Polyanionic Inhibitors of Hyaluronidase", *Biochim. Biophys. Acta* 13: 293–294.

Beiler, J. M., et al., (1948) "Inhibition of Hyaluronidase Action By Derivatives of Hesperidin", *J. Bio. Chem.*, 174:31–34.

Joyce, C. L., et al., (1986) "Effect of Hyaluronidase β–Glucuronidase and β–N–Acetylglucosaminidase Inhibitors on Sperm Penetration of the Mouse Oocyte", *Biol Reprod.*, 35:336–346.

Parkes, A. S., et al. (1954) "Biological and Biochemical Aspects for the Prevention of Fertilization By Enzyme Inhibitors", *Proc. Soc. Study Fertility*, 6:65–80.

(List continued on next page.)

*Primary Examiner*—Thurman K. Page
*Assistant Examiner*—Robert M. Joynes
(74) *Attorney, Agent, or Firm*—Fitch, Even, Tabin & Flannery

(57) ABSTRACT

Antimicrobial and contraceptive compositions and methods which prevent and/or reduce the risk of transmission of sexually transmitted diseases through sexual activity as well as prevent and/or reduce the risk of pregnancy are provided. The compositions contain (1) a matrix-forming agent, (2) a bio-adhesive agent, (3) a buffering agent, (4) optionally a humectant, (5) optionally a preservative, and (6) water; wherein the composition is suitable for application within the vagina; wherein the compositions forms a semisolid matrix on contact with ejaculate (thereby trapping ejaculated microbes and spermatozoa); wherein the composition causes hardening of cervical mucus (thereby decreasing the probability of sperm entry); wherein the composition forms a bio-adhesive layer over vaginal surfaces (thereby preventing or reducing the risk of contact of STD-causing microbes with the vaginal surfaces); wherein the composition maintains an acidic vaginal pH of less than about 5 in the presence of semen ejaculated from the male; and wherein the composition does not significantly impair the natural microbiological balance within the vagina. The antimicrobial and contraceptive compositions may also contain additional antimicrobial and/or contraceptive agents (e.g., nonoxynol-9, octoxynol-9, benzalkonium chloride, phosphorylated hesperidins, sulfonated hesperidins, polystyrene sulfonates, substituted benzenesulfonic acid formaldehyde co-polymers, $H_2SO_4$-modified mandelic acids, povidone iodine, itraconazole, ketoconazole, metronidazole, clotrimazole, fluconazole, teraconazole, miconazole, tinidazole, iconazole, chloramphenicol, nystatin, cyclopiroxolamine, and the like).

36 Claims, No Drawings

OTHER PUBLICATIONS

Joyce, C. L., et al., (1985) "Vaginal contraceptive activity of hyaluronidase and cyclooxygenase (prostaglandin synthetase) inhibitors in the rabbit", *Fertil. Steril.*, 44:426–428.

Joyce, C. L., et al., (1979) "Contraceptive Effects of Intravaginal Application of Acrosin and Hyaluronidase Inhibitors in Rabbit", *Contraception*, 19(1):95–106.

Martin, G. J., et al., (1952) "Effect of Phosphorylated Hesperidin, a Hyaluronidase Inhibitor, on Fertility in the Rat", *Science*, I 1 5:402.

Sieve, F., (1952) "A new antifertility factor." *Science*, 116:373–385.

Chang, M. C., et al., (1953) "Does Phosphorylated Hesperidin Affect Fertility?" *Science*, 117:274–276.

Thompson, R. Q., et al., (1953) "Effect of phosphorylated hesperidin and other flavonoids on fertility in mice.", *Science*, 118:657.

Homm, R. E., et al., (1985) ORF 13904 A new long–acting vaginal contraceptive. *Contraception*. 32: 267–275.

Foldesy, R. G., et al., (1986), "Multiple actions of a novel vaginal contraceptive compound", ORF 13904. *Fert.*

Won Hahn, D., et al. (1986), "Prototype of a new long–acting spermistatic agent", *Male Contraception: Advanced and Future Prospects*, Harper & Row, Hagerstown, pp. 218–226.

Mohan, P., (1992), "Anti–AIDs Development: Challenges and Strategies", *Pharmaceutical Research*, vol. 9, No. 6, pp. 703–714.

Mandell, G. L., et al., *Principles and Practice of Infectious Diseases*, vol. 1, Ch. 95, pp. 1218–1235 ($5^{th}$ Edition, 2000).

Breen, J., *The Gynecologist and the Older Patient*, (ed.) p. 304–305 (1988).

Berkow, R. (Editor–in–Chief), *The Merck Manual of Medical Information: Home Edition*, (1997), pp. 1081–1083.

Amaral, et al., "Study of the Vaginal Tolerance to Acidform, an Acid–Buffering Bioadhesive Gel", *Contraception*, 1999:60, pp. 361–366.

Philenko et al., "Anti–HSV Activity of Acidform", abstract presented in Jul. 1999 at the Thirteenth Meeting of the International Society for Sexually Transmitted Diseases Research.

Philenco et al., "Anti–chlamydia Activity of Acidform" abstract presented in Jul. 1999 a the Thirteenth Meeting of the International Society for Sexually Transmitted Diseases Research.

Andersch, et al., "Treatment of Bacterial Vaginosis with an Acid Cream: A Comparison between the Effect of Lactate–Gel and Metronidazole", *Gynecol. Obstet. Invest.*, 21: 19–25 (1986).

Bentley, et al., "Acceptability of a Novel Vaginal Microbicide During a Safety Trial Among Low–Risk Women", *Family Planning Perspectives*, vol. 32, No. 4, Jul./Aug. 2000.

\* cited by examiner

COMPOSITIONS AND METHODS FOR TRAPPING AND INACTIVATING PATHOGENIC MICROBES AND SPERMATOZOA

RELATED APPLICATION

This application is based on, and claims benefit of, U.S. Provisional Application Serial No. 60/187,574, filed on Mar. 7, 2000.

FIELD OF THE INVENTION

This invention generally relates to compositions and methods for preventing the transmission of sexually transmitted diseases (STDs) and/or reducing the rate of transmission of such sexually transmitted diseases in sexually active individuals. This invention also generally relates to compositions and methods for preventing conception and/or reducing the risk of conception in sexually active females. Although not wishing to be bound by theory, it is believed that the compositions of the present invention, when used within the vagina during sexual intercourse, tend to physically trap and inactivate pathogenic microbes associated with STDs as well as spermatozoa contained in ejaculate that may be deposited within the vagina. The present compositions and methods are especially effective for preventing, or reducing the likelihood of, conception in sexually active females and reducing the risk of being infected by, or of transmitting, sexually transmitted diseases during male/female sexual intercourse. It can, however, be used by heterosexual, homosexual, and bisexual individuals to reduce the risk of being infected by, or of transmitting, a sexually transmitted disease through sexual contact. The present method of this invention is especially effective when used in conjunction with so-called "safe sex" techniques.

The method of this invention generally comprises application of an effective amount of the trapping gel within the vagina. Although an applicator can be used to apply the trapping gel within the vagina, such an applicator would be removed before the sexual activity. Preferably, the trapping gel is applied before sexual activity. Although perhaps not as effective, it can also be applied after sexual activity; such delayed application should take place as soon as possible after the sexual activity. Increased protection can be obtained by application of the trapping gel both just before and just after the sexual activity. Although the present trapping gel is designed to provide anti-STD activity during heterosexual activity, it may also provide protection against STDs during other sexual activity (e.g., heterosexual or homosexual anal sex); throughout this specification, a reference to heterosexual intercourse is intended to include other forms of sexual activity.

The trapping gels of the present invention have both antimicrobial and contraceptive activities. The antimicrobial and contraceptive formulations of the present invention generally have fewer side effects than conventional vaginal contraceptives (e.g., nonoxynol-9). For example, the trapping gels useful in this invention are generally not toxic (or only slightly toxic) at their effective levels to natural and beneficial vaginal flora and, thus, do not significantly upset the local microbiological balance. Of course, inclusion of contraceptives such as nonoxynol-9 in the present trapping gels will increase the risk of side effects. Generally, however, such contraceptives can generally be added to the present compositions at lower levels than found in conventional vaginal contraceptives while maintaining their effectiveness. Furthermore, the present compositions are generally not cytotoxic (or at least only minimally so) and do not cause irritation or lesions of the vagina or cervix. In addition, the trapping gels of the present invention assist in maintaining the pH level within the vagina at natural acidic levels (generally about pH of about 3.5 to 4.5) and, therefore, provide even more protection. Maintaining the pH at such acidic levels reduces the risk of conception as well as infection by STD-causing microbes while maintaining local microbiological balance. Moreover, by reducing the risk of damage to the vaginal lining, the risk of infection by STDs, including HIV, is further reduced. Additionally, the trapping gels of this invention may be used to prevent and/or treat vaginitis and/or bacterial vaginosis.

When semen is ejaculated into the vagina, the trapping gel of the present invention causes thickening of the gel/semen mixture, forming a semisolid structure from which ejaculated pathogenic microbes (e.g., STD-causing microbes, including HIV) and spermatozoa cannot escape, or do so only slowly, thereby preventing or significantly reducing migration through the lower genital tract. The trapping gel also tends to harden cervical mucus, thereby preventing or decreasing sperm penetration of the vaginal mucus and obstructing passage through the cervical canal. Additional prevention of STD-infection by the trapping gel arises from the formation of a bio-adhesive, protective barrier over the vaginal lining (e.g., the stratified squamous epithelium) or over the rectal lining in the case of anal sex. To further increase the anti-STDs and/or contraceptive activity of the trapping gels of this invention, microbiocides and/or spermicides (e.g., nonoxynol-9 and others) can be included in the present formulations. It is expected that lower levels of such microbiocides and/or spermicides can be used in the present compositions and methods while maintaining high contraceptive activity, thereby reducing the side effects of such microbiocides and/or spermicides.

BACKGROUND OF THE INVENTION

In recent years, sexually transmitted diseases (STDs) have become an increasing medical problem and concern throughout the world. The HIV/AIDS epidemic over the last decade or so has significantly and dramatically underscored the threat of STDs to the human population. The best, and perhaps only realistic, approach to this increasing problem of STDs (especially HIV/AIDS) appears to be reducing the risk of transmission of STDs by pathogenic organisms and thus reducing the number of individuals who become newly infected. Even when treatments or cures become available, prevention of infections in the initial instance will likely remain as the first line of defense. For medical, psychological, and economic reasons, it is preferable to prevent the initial infection rather than treating, and even curing, individuals with STDs.

At present, education in regard to STDs, their modes of transmission, and so-called "safe-sex" techniques has, at least to some degree in the more developed countries, shown promise in reducing the risks of STD transmission through sexual activity. Screening of the blood supply has helped to reduce the risk of transmission of such STD-causing organisms via blood transfusions and related medical practices. Nonetheless, the spread of such STDs has not been halted to a satisfactory degree even in developed countries with active and progressive education programs. Even with their known effectiveness in preventing STDs, current safe-sex techniques are not always used, or are not always used properly, for many reasons (e.g. carelessness, lack of knowledge, improper techniques, cultural barriers, unplanned or spontaneous sexual activity, and the like). Moreover, even when used, safe-sex techniques (except perhaps abstinence) are not always effective. For example, condoms are generally only about 80 to about 90 percent effective in preventing conception when used alone; in the case of such failures, STD-causing organisms, if present, may pass from one sexual partner to the other.

Various birth control devices—including barrier methods and vaginal contraceptives—are currently available. Some of these may, in addition, also have at least some degree of anti-STD activity. For example, condoms can help prevent the transmission of STDs so long as they are properly used and/or they perform properly. Nonoxynol-9, currently one of the most widely used contraceptive agents, is reported, at least in some cases, to reduce the risk of transmission of some STDs. Nonoxynol-9, which is a nonionic detergent with strong surfactant properties, acts, like most other chemical-based contraceptives, by killing or otherwise immobilizing spermatozoa (e.g., spermicidal activity). Nonoxynol-9 is a potent cytotoxic agent which tends to nonspecifically disrupt cell membranes. These properties, however, give rise to some very significant disadvantages. Nonoxynol-9 can injure vaginal/cervical epithelial and other cells at concentrations as low as about 0.0005 percent (in vitro). Clinical studies have confirmed epithelial disruption of the vagina and cervix at the concentrations normally present in vaginal contraceptive formulations (generally greater than about 3 percent nonoxynol-9). Nonoxynol-9 also disrupts the normal vaginal flora which provides a protective mechanism, perhaps by maintaining a low pH, to guard against the invasion of pathogenic microbes. Nonoxynol-9 may also partially dissolve or remove the protective glycoprotein coating in the vagina. The cytotoxic, flora-disruptive, and glycoprotein-removal effects of nonoxynol-9 can lead to vaginal damage or injury, including lesions. Some women are especially sensitive to nonoxynol-9 and manifest these effects with only occasional use. The disruption of these protective mechanisms by nonoxynol-9 can actually increase the risks of STD infections since the breakdown of the protective mechanisms, and especially the occurrence of lesions, allows STD-causing organisms an easier pathway into the cells. Additionally, the disruption of these protective mechanisms by nonoxynol can increase the risk of vaginitis and/or bacterial vaginosis.

Of course, various commercial vaginal creams and ointments are currently available over the counter or by prescription or are in various stages of development. Nonoxynol-9, octoxynol-9, and benzalkonium chloride are generally available as suppositories, inserts, creams, films, foams, and gels. Examples of such commercial products include, for example, K-Y Plus™ (2.2 percent nonoxynol-9; Advanced Care Products, Raritan, N.J.); Encare™ (3 percent nonoxynol-9; Thompson Medical Co., West Palm Beach, Fla.); Gynol II (Advanced Care Products, Raritan, N.J.); Ortho Options Conceptrol (Advanced Care Products, Raritan, N.J.); Semicid (Whitehall Robbins Healthcare, Madison, N.J.); and Advantage-S (Columbia Laboratories, Aventura, Fla.). As discussed above, the levels of nonoxynol-9 or other cytotoxic agents contained in such products are generally disruptive to the vagina and cervix and upset the normal vaginal milieu. Moreover, such formulations have only limited capability, if any, to prevent STD infections. Indeed, many women using such products report burning and pain sufficient to terminate the use of the products. Gels designed to control vaginal pH are also available. For example, Aci-Jel™ (Ortho-McNeil Pharmaceutical Corp., Raritan, N.J.) is a water-dispersible buffered gel having a pH of 3.9 to 4.1 which is used to restore and maintain normal vaginal acidity. Such gels are designed to control vaginal pH and are not designed to prevent STDs and/or conception; these gels do not trap and/or inactivate STD-causing pathogens or spermatozoa.

U.S. Pat. No. 5,439,685 (Aug. 8, 1995) provides a pharmaceutical composition for the prevention of sexually transmitted diseases. These compositions are reported to produce a film or barrier layer over the vagina mucosa which prevents contact of the STD-causing microbes with the vagina surfaces. However, these formulations do not form a semisolid matrix with the ejaculate to effectively trap STD-causing microbes and/or spermatozoa; nor do they cause hardening of cervical mucus to prevent entry of spermatozoa. These gels may also contain cytotoxic agents such as nonoxynol-9, benzalkonium chloride, and sodium cholate which, which in spite of the film or barrier, may still be disruptive to the vagina and cervix. Finally, these gels are designed to be used in conjunction with a vaginal device such as a tampon, unlike the present invention.

More recently, BufferGel™ (ReProtect LLC, Baltimore, Md.), developed at John Hopkins University, is undergoing clinical trials. BufferGel™ is reported to be a negatively charged, non-absorbable high molecular weight polymer gel, designed to maintain vaginal pH below 5 in the presence of semen. As detailed in U.S. Pat. No. 5,617,877 (Apr. 8, 1997), BufferGel™ relies on a polymer comprised of carboxylated monomers (preferably crosslinked polyacrylic acids such as, for example, Carbopol® polymers (high molecular weight homo- and co-polymers of acrylic acid crosslinked with a polyalkenyl polyether; available from B F Goodrich)) to control the vaginal pH. BufferGel™ does not trap STD-causing microbes and/or ejaculated spermatozoa or harden cervical mucus, thereby allowing the STD-causing microbes and/or ejaculated spermatozoa to readily migrate throughout the lower genital tract. Moreover, the composition is designed to be used with a device to be inserted into the vagina and positioned covering the cervix. To be effective, the device must remain in position covering the cervix. Removal of the device or a shift of its position relative to the cervix can destroy, or at least significantly reduce, its effectiveness. As detailed in the patent, the "device positions advantageous quantities of appropriate buffers in a dome shaped configuration that provides stable positioning of the device around the cervix. The large surface area of the device and its resilient circular shape cause it to project into the posterior vaginal fornix, gently spreading the vaginal mucosa against the surface of the device, thus preventing pooling of the ejaculate in a relatively inaccessible cul-de-sac. The device is highly absorptive, and rapidly sequesters and acidifies both semen and menstrual fluid." Of course, the use of such devices in combination with BufferGel™ requires significant skill and motivation by the user to obtain, and maintain, proper placement of the device. Moreover, there is likely to be a reduction of pleasure and sensitivity of the sex act using such a device. Such devices are, therefore, less likely to be used on a consistent basis because of the difficulty of use, especially in cases of "spontaneous" sexual activity.

Similar crosslinked polyacrylic acids (i.e., polycarbophil) have also been used for drug (e.g., nonoxynol-9 or progesterone) delivery within the vagina. Robinson et al., *J. Controlled Release*, 28, 87 (1994).

It would be desirable, therefore, to provide improved compositions and methods which reduce the risk of STD transmission and/or infections during sexual activity. It would also be desirable if such improved compositions and methods also possess contraceptive activity. It also would be desirable if such compositions and methods would not interfere with the natural and protective vaginal mechanisms. It also would be desirable if such compositions and methods can be used to prevent and/or treat vaginitis and/or bacterial vaginosis. It would also be desirable if such compositions and methods would be relatively easy to use and have significantly fewer side effects than currently available methods (i.e., nonoxynol-9 at relatively high levels) so that it would more likely be used on a consistent basis. It would also be desirable if such compositions and methods did not require a physical device to remain within the vagina during use. The present invention, as detailed in the present specification, provides such methods.

SUMMARY OF THE INVENTION

This invention generally relates to compositions and methods which prevent and/or reduce the risk of transmission of sexually transmitted diseases through sexual activity and which are also contraceptive. This method is especially suitable for use by heterosexual couples for preventing pregnancy and significantly reducing the risk of being infected by, or of transmitting, a STD through sexual contact. Although this method can be used alone, it is generally preferred that it be used in conjunction with other so-called "safe sex" techniques in order to even further reduce the risk of pregnancy and/or STD transmission or infection.

The method of this invention generally comprises the application of an effective amount of the compositions of this invention within the vagina prior to engaging, or as soon as possible after engaging, in sexual activity. The compositions of this invention, in addition to anti-STD activity, act as vaginal contraceptives and generally have fewer side effects than conventional vaginal contraceptives (e.g., nonoxynol-9). The compositions of this invention are designed to form a semisolid matrix when they come in contact with semen ejaculated into the vagina. The semisolid matrix is effective in trapping STD-causing microbes, including HIV, and spermatozoa, and thereby preventing or greatly decreasing their migration through and out of the lower genital tract. Contraceptive activity is further enhanced by making the formulation hypertonic which results in hardening of the cervical mucus, thereby preventing or hindering entry of spermatozoa into the cervix. As those skilled in the art realize, a hypertonic solution or gel generally has a higher level of salts than a reference solution. For purposes of the present invention, the reference solution is normal reproductive tract fluids or vaginal mucus. Reproductive tract fluids generally have an osmolality of about the same as, or higher than, blood plasma and generally in the range of about 300 to about 350 mosmoles/kg. The osmolality of cervical mucus will vary somewhat during the cycle since it becomes thinner during the midcycle (ovulatory period when sperm passage occurs) and thicker during the anovulatory period. If desired, the osmolality of gel can be measured using an osmometer.

Prevention of STD transmission and infection is further enhanced by inclusion of bio-adhesive agents which can form a bio-adhesive film over the vaginal and cervical surfaces (as well as rectal surfaces during anal sex), preventing contact of STD-causing microbes with the walls of the lower genital tract. Finally, the compositions of the present invention help in maintaining a natural pH balance within the vagina even in the presence of semen (normal pH of semen is about 7.2 to 7.8; neutral to slightly basic). Vaginal pH is reported to increase from about 4 to about 6 to 7 shortly after ejaculation during unprotected sex and remains at such high levels for two to eight hours. Reestablishing or maintaining an acidic pH appears to assist in killing, inactivating, and/or immobilizing certain STD-causing microbes (including HIV) and spermatozoa within the vagina, thereby preventing or reducing the risk of STD transmission or infection. Reestablishing or maintaining an acidic pH within the vagina also assists in maintaining the natural and beneficial vaginal flora. Moreover, the protective glycoprotein vaginal coating is not significantly disrupted or impaired. Disruption of the natural vaginal flora and/or removal or disruption of the protective glycoprotein vaginal coating using conventional vaginal contraceptives can lead to irritation of the vaginal wall and/or lesions on the vaginal wall which can make the transmission of STD easier and/or more likely.

The trapping gels of the present invention have a number of other attributes which make them especially useful as anti-STDs agents and/or contraceptives. For example, the gels can be formulated to provide gels which are thick, viscous, smooth, pleasant to feel, and pleasantly acidic in taste. The gels are also water dispersible but retain their viscosity when diluted. The trapping gels of the present invention can also be formulated in rapidly dispersible solid forms (e.g., powders, tablets, and the like; see Example 11) which, when inserted into the vagina, form the desired trapping gel by rapidly disintegrating or dispersing through the action of vaginal or other fluids present within the vagina. Such solid forms are, of course, especially convenient for carrying, for example, in a purse. Of course, other dosage forms of the trapping gels can be used if desired. Suitable dosage forms include, for example, gels, creams, lotions, viscous liquids, tablets, powders, films, suppositories, foams, and the like. Although solid forms (e.g., tablets and powders) will generally contain only small amounts of water, the vaginal or other fluids within the vagina can supply the desired water to form the trapping gel composition. The major components are generally considered safe (U.S.P.-listed or GRAS-listed). The gels can be easily dispensed through a syringe or similar applicator or applied manually or can be in the form of tablets or other solid forms for insertion into the vagina. The gels are designed to provide a controlled release of any active ingredients (e.g., nonoxynol-9) and, therefore, are expected to provide long term efficacy. Through their humectant activity, the gels also increase the moisture level of the vagina, thereby reducing the occurrence of vaginal lesions and increasing the pleasurable aspects of the sexual activity. The gels may also contain lubricants which will also increase the pleasurable aspects of the sexual activity. The gels should also reduce leakage and avoid messiness. Many of the just-mentioned aspects and benefits of the present gel compositions and methods will encourage consistent use, thereby providing even further protection. The gels are also useful as delivery systems for active ingredients with antimicrobial and/or contraceptive properties.

One object of the present invention is to provide an antimicrobial and contraceptive composition that reduces the risk of transmission of, or infection by, a sexually transmitted disease through sexual activity involving a vagina of a female and a penis of a male, said composition comprising (1) a matrix-forming agent, (2) a bio-adhesive agent, (3) a buffering agent, and (4) water; wherein the composition is suitable for application within the vagina; wherein the composition forms a semisolid matrix on contact with semen; wherein the composition causes hardening of cervical mucus; wherein the composition forms a bio-adhesive layer over vaginal surfaces; wherein the composition maintains an acidic vaginal pH of less than about 5 in the presence of semen ejaculated from the male (e.g., before, during, or after the sexual activity); wherein the composition does not significantly impair the natural microbiological balance within the vagina; and wherein the composition is hypertonic. If desired, the antimicrobial and contraceptive composition may also include additional antimicrobial and/or contraceptive agents (e.g., nonoxynol-9, octoxynol-9, benzalkonium chloride, phosphorylated hesperidins, sulfonated hesperidins, polystyrene sulfonates, substituted benzenesulfonic acid formaldehyde co-polymers, and $H_2SO_4$-modified mandelic acids, povidone iodine, itraconazole, ketoconazole, metronidazole, clotrimazole, fluconazole, teraconazole, miconazole, tinidazole, iconazole, chloramphenicol, nystatin, cyclopiroxolamine, and the like). Preferably the antimicrobial and contraceptive composition also contains a humectant, a preservative, and/or a lubricant.

Another object of the present invention is to provide a method of reducing the risk of transmission and infection by a sexually transmitted disease through sexual activity involving a vagina of a female and a penis of a male, said method comprising administering an effective amount of an antimicrobial and contraceptive composition within the vagina prior to, or shortly after, sexual activity; wherein the composition comprises (1) a matrix-forming agent, (2), a bio-adhesive agent, (3) a buffering agent, and (4) water; wherein the composition is suitable for application within the vagina; wherein the composition forms a semisolid matrix on contact with semen; wherein the composition causes the hardening of cervical mucus; wherein the composition forms a bio-adhesive layer over vaginal surfaces; wherein the composition maintains an acidic vaginal pH of less than about 5 in the presence of semen ejaculated from the male; wherein the composition does not significantly impair the natural microbiological balance within the vagina (e.g., before, during, or after the sexual activity); and wherein the composition is hypertonic. If desired, the composition may also include additional antimicrobial and/or contraceptive agents (e.g., nonoxynol-9, octoxynol-9, benzalkonium chloride, phosphorylated hesperidins, sulfonated hesperidins, polystyrene sulfonates, substituted benzenesulfonic acid formaldehyde co-polymers, and $H_2SO_4$-modified mandelic acids, povidone iodine, itraconazole, ketoconazole, metronidazole, clotrimazole, fluconazole, teraconazole, miconazole, tinidazole, iconazole, chloramphenicol, nystatin, cyclopiroxolamine, and the like). Preferably the antimicrobial and contraceptive composition also contains a humectant, a preservative, and/or a lubricant.

Still another object of the present invention is to provide an antimicrobial and contraceptive composition for reducing the risk of transmission and infection by a sexually transmitted disease through sexual activity comprising (1) about 1 to about 10 percent of one or more matrix-forming agents, (2) about 1 to about 10 percent of one or more bio-adhesive agents, (3) about 1 to about 10 percent of one or more buffering agents, and (4) water; wherein the composition is suitable for application in a vagina; wherein the composition forms a semisolid matrix on contact with semen ejaculated from a male into the vagina; wherein the composition causes hardening of cervical mucus of the vagina; wherein the composition forms a bio-adhesive layer over vaginal surfaces; wherein the composition maintains an acidic vaginal pH of less than about 5 in the presence of semen ejaculated from the male; wherein the composition does not significantly impair the natural microbiological balance within the vagina (e.g., before, during, or after the sexual activity); and wherein the composition is hypertonic. If desired, the antimicrobial and contraceptive composition may also include additional antimicrobial and/or contraceptive agents (e.g., nonoxynol-9, octoxynol-9, benzalkonium chloride, phosphorylated hesperidins, sulfonated hesperidins, polystyrene sulfonates, substituted benzenesulfonic acid formaldehyde co-polymers, and $H_2SO_4$-modified mandelic acids, povidone iodine, itraconazole, ketoconazole, metronidazole, clotrimazole, fluconazole, teraconazole, miconazole, tinidazole, iconazole, chloramphenicol, nystatin, cyclopiroxolamine, and the like). Preferably the antimicrobial and contraceptive composition also contains a humectant, a preservative, and/or a lubricant.

These and other advantages of the present invention will be apparent from a consideration of the present specification.

DETAILED DESCRIPTION OF THE INVENTION

The present invention relates to a trapping gel that, when placed in a body orifice (e.g., vagina), entraps and inactivates spermatozoa and/or sexually transmitted disease (STD)-causing microbes. Although not wishing to be limited by theory, it appears that the formulations of this invention form a semi-hardened or semisolid matrix when exposed to an ejaculate, thereby sequestering spermatozoa and STD-causing microbes. Additionally, the formulations of this invention form a bio-adhesive and essentially impenetrable layer over the surface of the orifice (e.g., vagina and cervical tissue), preventing contact and/or entry of spermatozoa and/or STD-causing microbes. The formulations of this invention are hypertonic; thus, when placed in the vagina, it will sequester water from the mucus in the cervix, and thereby cause the mucus to harden and provide even further protection by preventing or significantly reducing entry of spermatozoa and/or STD-causing microbes into the cervix. These properties, working together, allow for effective entrapment of spermatozoa and/or STD-causing microbes within the vagina and effectively prevent such spermatozoa and/or STD-causing microbes from entering the body either through the vaginal lining or the cervix. The formulation is acid-buffering to maintain the normal vaginal milieu and environment which further assists to inactivate certain STD-causing microbes and spermatozoa; maintaining the normal vaginal milieu also assists in maintaining the body's natural defenses against certain STD-causing microbes. The formulation may contain sperm- and/or STD microbe-inactivating ingredients such as spermicides and/or microbiocides. The entrapment or immobilization of the spermatozoa and/or STD-causing microbes within the vagina by the formulations of the present invention allows such sperm- and STD microbe-inactivating ingredients sufficient time to more completely inactivate the spermatozoa and/or STD-causing microbes that may be present. The formulations of this invention may also be used to prevent and/or treat vaginitis and/or bacterial vaginosis.

Compositions and methods are provided for (1) prevention and/or reducing the rate or probability of transmission of sexually transmitted diseases between sexual partners when one or more of the partners is infected and (2) prevention and/or reducing the risk of pregnancy. Although it is mainly directed at heterosexual conduct (i.e., male/female vaginal intercourse), the compositions of this invention may also be used by parties engaged in other types of sexual conduct. For example, the compositions of this invention could be used by parties engaged in anal intercourse (male/female or male/male); compositions of this invention intended to be used in anal intercourse are preferably modified to adjust the buffering capacity to pH values normally found in the rectum and by using higher levels of lubricants. Of course, the present method is not limited to use by sexual partners where one of the partners is known to be infected by a STD or at risk for a STD. Rather, this method can be used by sexual partners where neither has a known STD, where one partner has a STD or is at risk for a STD, or where both partners have STDs or are at risk for STDs. Because STDs can be transmitted by an infected partner even before symptoms appear in that party, it is generally recommended that this method be used consistently by sexually active individuals. Of course, since the compositions are contraceptive, they can be use by heterosexual couples where the avoidance of conception is also desired. Moreover, since no one method of preventing the transmission of STDs and/or conception—except perhaps complete avoidance of sexual activity—is completely effective, the present method is preferably practiced in conjunction with other methods of reducing the probability of transmission of STDs and/or conception. For example, the present method can be combined with the use of condoms (male or female) and other safe-sex techniques to significantly improve the overall effectiveness as compared to the use of either method alone; such combined methods could go a long way towards eliminating or, at least, significantly reducing the transmission of STDs from one sexual partner to another.

Preventing the initial infection (or reducing the risk of infection), as opposed to treatment of the STD after infection, is critically important medically, psychologically, and economically. Especially for STDs such as HIV/AIDS where there is no known cure, the importance of prevention cannot be overstated. Moreover, as those skilled in the art will realize, the prevention of a disease is generally very different from, and much preferred, as compared to a cure or treatment for the disease (if such cure is even available). For example, AZT and other HIV/AIDS drugs can slow the progression of the disease (and, in some cases and with the use of other strategies, prevent transmission from a HIV-positive woman to her unborn child), but they are not capable of curing the disease. Except in the limited example of an infected mother and her unborn child, the use of such drugs as AZT before the initial infection would not be medically or economically sound practice and would not reduce the risk of infection without subjecting such uninfected individuals to undesired side effects typically associated with the use of these relatively toxic drugs. Likewise, preventing an undesired pregnancy in the first instance, rather than later resorting to medical procedures to terminate the pregnancy, would have significant medical, psychological, and economic, advantages.

The method of the present invention is carried out by applying an effective amount of the trapping gel of the present invention within the vagina. For purposes of this invention, an "effective amount" is an amount of the composition sufficient to (1) cause entrapment of STD-causing microbes and spermatozoa from the ejaculate, (2) form a bio-adhesive film over vaginal surfaces, and (3) maintain a low or acidic pH within the vagina before or after a typical or normal ejaculation by the male during sexual intercourse. A single dose will normally be in the range of about 1 to about 8 ml of the trapping gel; preferably the single dose is about 3 to about 5 ml. Of course, doses higher or lower than these amounts can be used if desired. For purposes of this invention, a "low or acidic pH within the vagina" is generally considered to be within the normal pH level of a healthy female. Preferably, such an acidic pH is less than about 5; more preferably such an acidic pH is in the range of about 3.5 to about 4.5. In other words, besides providing effective entrapment of STD-causing microbes and spermatozoa and the formation of a protective layer of vaginal surfaces, the effective amount of the composition of this invention is an amount which provides sufficient buffering capacity to maintain the pH of the vagina in a low or acidic pH condition in the presence of a typical amount (normally about 1 to about 5.0 ml) of semen from a single "normal" ejaculation having an alkaline pH in the range of about 7.2 to about 7.6. The compositions of this invention are also hypertonic (i.e., having a higher water activity or osmotic pressure relative to the mucus in the cervix in normal, healthy females). Generally, reproductive tract fluids, including cervical mucus, are generally expected to have an osmolality similar to that of blood plasma (normally in the range of from about 290 to about 320 mosmoles/kg). Thus, the osmolality of the trapping gels of this invention, as measured using conventional osmometer, should be higher than the normal osmolality of blood plasma. Although the compositions of this invention are mainly intended to be used in situations where the vagina has a normal pH, it can also be used in cases where the microbiological vaginal balance has already been upset (e.g., active yeast infection); this buffering capacity may assist in returning the vagina to the desired pH range and a more healthy state. In other words, the compositions of this invention may, if desired, be used to prevent and/or treat, for example, vaginal infections, including, for example, vaginitis or bacterial vaginosis.

The trapping gels of the present invention may also be used with conventional birth-control or safe-sex devices. For example, the trapping gels could used in conjunction with condoms (i.e., via lubricants applied to the interior and/or exterior surfaces), diaphragms, cervix caps, or similar products. The trapping gels of the present invention could also, for example, be released into the vagina by hand, suppositories, or conventional tampon or syringe techniques. The method of administering or delivering the trapping gel into the vagina is not critical so long as an effective amount of the trapping gel is delivered into the vagina. The trapping gels of the present invention may also be used for protection during anal intercourse and can be applied using similar techniques.

The trapping gels of the present invention contain (1) a matrix-forming agent, (2) a bio-adhesive agent, (3) a buffering agent, and (4) water. More preferably, the trapping gels of the present invention contain (1) a matrix-forming agent, (2) a bio-adhesive agent, (3) a buffering agent, (4) a humectant, (5) a preservative, and (6) water. If desired, the composition may also include an antimicrobial and/or a contraceptive agent (e.g., nonoxynol-9, octoxynol-9, benzalkonium chloride, phosphorylated hesperidins, sulfonated hesperidins, polystyrene sulfonates, substituted benzenesulfonic acid formaldehyde co-polymers, and $H_2SO_4$-modified mandelic acids, povidone iodine, itraconazole, ketoconazole, metronidazole, clotrimazole, fluconazole, teraconazole, miconazole, tinidazole, iconazole, chloramphenicol, nystatin, cyclopiroxolamine, and the like). The trapping gels of the present invention generally contain (1) about 1 to about 10 percent of one or more matrix-forming agents, (2) about 1 to about 10 percent of one or more bio-adhesive agents, (3) about 1 to about 10 percent of one or more buffering agents, (4) 0 to about 2 percent of one or more humectants, (5) 0 to about 2 percent of one or more preservatives, (5) 0 to about 10 percent of one or more antimicrobial or contraceptive agents, and (7) water. More preferably, the trapping gels of the present invention contain (1) about 3 to about 5 percent of one or more matrix-forming agents, (2) about 2.5 to about 6 percent of one or more bio-adhesive agents, (3) about 1 to about 7 percent of one or more buffering agents, (4) about 6 to about 10 percent of one or more humectants preservatives, (5) about 0.1 to about 1 percent of one or more preservatives, (6) about 0.2 to about 5 percent of one or more antimicrobial or contraceptive agents, and (7) water.

Gelling or matrix-forming agents suitable for use in the present invention should be stable over a wide pH range, especially over the normal acidic pH values found in the vagina. Suitable matrix-forming agents include, for example, alginic acid, chitosan, gellan gum, poloxamer, and the like. Alginic acid is the preferred gel hardening or matrix-forming agent and is a generally linear glycouronan polymer containing a mixture of -(1,4)-D-gulosyuronic acid and -(1,4)-D-gulosyuronic acid residues. Generally, the molecular weight of the alginic acid is the range of about 20 to about 300,000 g/mole, preferably in the range of about 20,000 to about 250,000 g/mole, and most preferably about 240,000 g/mole. Alginic acid is expected to form insoluble alginates by interacting with monovalent and divalent cations (especially $Na^+$, $K^+$, and $Ca^{++}$) in seminal plasma. Since vaginal fluids generally contain very little $Ca^{++}$, the semisolid matrix is formed only when ejaculate is present. In such cases, the semisolid matrix will trap STD-causing microbes and spermatozoa so that they cannot migrate through the lower female genital tract. Alginates also swell in contact with water, thereby assisting in maintaining the desired gel or matrix structure within the vagina. Of course, alginic acid or salts of alginic acid may also contribute to the acid buffering activity of the trapping gels of the present invention since they have a pH of about 1.5 to about 3.5 in an aqueous solution. Alginic acid may also contribute to the bioadhesive nature of the present formulations and, therefore, assist in providing bioadhesive activity. Because of its high molecular weight, alginic acid will not be absorbed by the body. Thus, its matrix-forming, bioadhesive, and acid-buffering properties will be maintained so as long as the gel remains in the vagina. Moreover, due to the innate bio-adhesive properties of the trapping gel, it will normally remain within the vagina for about 12 to 24 hours (or even longer) if not removed by the woman.

Bio-adhesive agents suitable for use in the present invention include, for example, xanthan gum, hydroxypropyl cellulose, hydroxypropyl methyl cellulose, sodium carboxymethyl cellulose, chitosan, polycarbophil, carbopol, and the like. The preferred bio-adhesive gum is xanthan gum, a high molecular weight polysaccharide gum containing D-glucosyl, D-mannosyl, and D-glucosyluronic acid residues and varying proportions of O-acetyl and pyruvic acid acetal. The primary structure is a cellulose backbone with trisaccharide side chains; the repeating unit is a pentasaccharide. Generally the molecular weight is greater than about $10^6$ g/mole. Hydroxyethyl cellulose is preferably used in trapping gels that do not contain nonoxynol-9.

Buffering agents are used in the present trapping gel to maintain the pH of the vagina within its normal acidic range (i.e., a pH of less than about 5 and more preferably in the range of about 3.5 to about 4.5) even in the presence of normal amounts of ejaculate. Suitable buffering agents include, for example, lactic acid, citric acid, potassium acid tartrate, benzoic acid, alginic acid, sorbic acid, fumaric acid, ascorbic acid, stearic acid, oleic acid, tartaric acid, edetic acid ethylenediaminetetracetic acid, acetic acid, malic acid, and the like. The acids may be added as free acids, hydrates, or pharmaceutically acceptable salts. Generally the free acids are preferred. Of course, the free acids can be converted to the corresponding salts in situ (i.e., within the vagina). It is generally preferred that several buffering agents are included in the trapping gel of this invention to provide increased buffering capacity. Alginic acid, of course, can function as both a matrix-forming agent and a buffering agent in the present trapping gels. Since alginic acid will not be absorbed by the body, its acid buffering effect will be longer lasting as compared to the other buffering agents which may be absorbed by the body.

The trapping gels of this invention may also include, and preferably do include, humectants. Suitable humectants include, for example, glycerol, polyethylene glycols, propylene glycols, sorbitol, triacetin, and the like. Glycerol, which is the preferred humectant, prevents the formation of a dry film on the gel when placed within the vagina. Glycerol may also act as a lubricant.

The trapping gels of this invention may also include, and preferably do include, a preservative. Suitable preservatives include, for example, benzoic acid, sodium benzoate, methylparaben, ethylparaben, butylparaben, propylparaben, benyalkonium chloride, phenylmercuric nitrate, chlorhexidine, and the like. The preferred preservative is benzoic acid. As discussed above, benzoic acid may also contribute to the buffering capacity of the gel.

The trapping gels of this invention preferably contain alginic acid as the matrix-forming agent; xanthan gum and/or hydroxycellulose as the bio-adhesive agent; a buffering agent selected from the group consisting of lactic acid, citric acid, benzoic acid, potassium acid tartrate; glycerol as the humectant; benzoic acid as the preservative; and water. More preferably, the trapping gels of this invention contain xanthan gum, alginic acid, lactic acid, citric acid, benzoic acid, potassium bitartrate, glycerol, and water. If additional antimicrobials and/or contraceptives are to be included, the trapping gels of the invention more preferably contain xanthan gum, alginic acid, lactic acid, citric acid, benzoic acid, potassium bitartrate, glycerol, water, and a antimicrobial and/or a contraceptive agent selected from the group consisting of nonoxynol-9, octoxynol-9, benzalkonium chloride, phosphorylated hesperidins, sulfonated hesperidins, polystyrene sulfonates, substituted benzenesulfonic acid formaldehyde co-polymers, and $H_2SO_4$-modified mandelic acids, povidone iodine, itraconazole, ketoconazole, metronidazole, clotrimazole, fluconazole, teraconazole, miconazole, tinidazole, iconazole, chloramphenicol, nystatin, and cyclopiroxolamine.

Suitable antimicrobial and contraceptive agents include, for example, nonoxynol-9, octoxynol-9, benzalkonium chloride, phosphorylated hesperidins, sulfonated hesperidins, polystyrene sulfonates, substituted benzenesulfonic acid formaldehyde co-polymers, $H_2SO_4$-modified mandelic acids, povidone iodine, itraconazole, ketoconazole, metronidazole, clotrimazole, fluconazole, teraconazole, miconazole, tinidazole, iconazole, chloramphenicol, nystatin, cyclopiroxolamine, and the like. Generally these antimicrobial and contraceptive agents, if used, are included in an amount of less than about 12 percent, and preferably at a level of about 2 to about 6 percent. Nonoxynol-9, a well known and commercially available contraceptive agent, may cause vaginal irritation in some women; in those cases it may be preferred to lower the concentration, or even eliminate, nonoxynol-9. Suitable phosphorylated hesperidins and sulfonated hesperidins are described in U.S. Pat. No. 5,925,621 (Jul. 20, 1999). Suitable $H_2SO_4$-modified mandelic acids are described in U.S. Pat. No. 5,932,619 (Aug. 3, 1999). Suitable substituted acid formaldehyde co-polymers are described in U.S. Pat. No. 6,028,115 (Feb. 22, 2000); especially preferred co-polymers include the branched poly(methyl ether)hydroquinone sulfonates and derivatives thereof. Suitable polystyrene sulfonates are described in U.S. patent application Ser. No. 09/252,417 (filed Feb. 18, 1999). These patents and patent applications are hereby incorporated by reference. Generally, acid-stable, noncytotoxic agents such as $H_2SO_4$-modified mandelic acids and branched poly(methyl ether) hydroquinone sulfonates and derivatives thereof, are preferred.

The trapping gels of this invention are prepared using conventional gel preparation techniques. It is important, however, to ensure that the buffering agents are fully solubilized in the final product and that the entrapment of air in the gel is avoided or at least kept to a minimum. To reduce the entrapment of air in the gel, it is generally preferred that the less hydrophilic agents (e.g., alginic acid) are added in small increments. Alternatively, the trapping gels of this invention can also be prepared in readily dispersable solid forms (e.g., powders, tablets, and the like) which can be converted to the desired gel consistency by action of aqueous based fluids external to or within the vagina when desired. As those skilled in the art will realize, the methods for preparing the trapping gels of this invention can be modified for batch, semi-continuous, or continuous operation so long as the resulting trapping gels have the desired and beneficial properties described herein.

For vaginal heterosexual intercourse, the trapping gel could be inserted into the vagina prior to intercourse. For anal intercourse (heterosexual or homosexual), the trapping gel could be insertted into the rectum prior to intercourse. For either vaginal or anal intercourse, the trapping gel could also act as a lubricant. For added protection it is generally preferred that the trapping gel be applied-before intercourse or other sexual activity and that, if appropriate, a condom be used. For even further protection, the trapping gel can be reapplied as soon as possible after completion of the sexual activity.

If desired, flavorants, scents, fragrances, and colorants can be incorporated into the trapping gel so long as they do not interfere with the protection afforded by the trapping gel. Indeed, incorporation of such flavorants, scents, fragrances, and colorants into the compositions of this invention may provide further protection by increasing the probability that the trapping gel will be used during sexual activity.

One advantage of the present method is that it can be used for protection during a wide variety of sexual activities (vaginal or anal) by heterosexuals, bisexuals, and homosexuals. Another advantage of the present method of reducing the transmission of STDs is that this method can be implemented and/or used most easily by the party being penetrated. Thus, a woman could use the present method to protect herself (as well as her partner) with or without the partner's knowledge of the method being used. Moreover, the partner would not be required to rely on his or her partner's claim of being STD-free or agreement to use condoms or other barrier devices for protection. Either or both sexual parties (especially the female participant) could initiate and implement the use of the present method prior to, or after, the sexual encounter. Preferably the method is used before the sexual activity and most preferably both before and after the sexual activity. Although use only after the sexual activity would provide less protection, it would still be desirable to implement this method afterwards if the method was not used prior to the sexual activity for any reason (e.g., in cases of rape). Of course, the sooner this method is initiated after the sexual activity the better. Preferably the method is initiated within one hour, more preferably within 15 minutes, and most preferably almost immediately after the sexual activity. Even after periods greater than these, however, the use of this method as soon as possible after the sexual activity may provide at least some protection (as compared to no treatment).

Still another advantage of the present invention is that, in contrast to other protective methods which rely only on a cytotoxic compound (e.g., nonoxynol-9), the trapping gel used in this invention does not significantly affect or inhibit the growth characteristics of the normal vaginal flora or otherwise significantly irritate the vaginal tissue when used at inhibitory, noncytotoxic, or clinical concentrations. This benefit is at least partially due to the absence of cytotoxic agents in the present compositions. Additionally, even when nonoxynol-9 is included in the present compositions, the adverse characteristics of nonoxynol-9 are less noticeable since (1) the required level of nonoxynol-9 can reduced since the trapping gel has its own contraceptive activity and (2) the bioadhesive nature of the composition affords protection of the vagina lining by reducing the contact of the nonoxynol-9 with the vagina lining. Thus, the beneficial components of normal vaginal flora are generally not disrupted by the use of the present invention. Significant inhibition or modifications of the vaginal flora or other irritations (such as when relatively high amounts of nonoxynol-9 are used in conventional contraceptives) can lead to increased risks of infections (both STD and non-STD types), unusual discharges, general discomforts, and the like, which, in turn, can lead to a reluctance to use or fully take advantage of the protective method. Moreover, the compositions offer the added benefit that they may also be used to prevent and/or treat vaginitis and/or bacterial vaginosis.

By avoiding or reducing the intensity of these effects on the vaginal flora and tissue, the present method is more likely to be used on a consistent basis. By reducing the number of unprotected sex acts (preferably to zero) and encouraging the use of the methods of this invention both before and after each sex act, the overall degree of protection should be significantly increased. By avoiding or reducing vaginal irritations and especially lesions on the vaginal walls (or rectum lining in the case of anal intercourse), the transmission of STD should be further reduced since transmission of STD-causing organisms is generally easier where damage to the cell walls has occurred. Thus, improvements in ease of use, reduction in side effects, ability to be initiated by the party to be penetrated, the ability to be used for different and varied sexual activities, and the ability to maintain normal vaginal flora during use give the compositions and methods of the present invention significant advantages as a contraceptive and/or anti-STD method.

The embodiments and examples described and discussed are intended to illustrate the present invention and not to limit the scope of the invention which is defined in the appended claims. Unless specified otherwise, all percentages are by weight.

EXAMPLE 1

Gels were prepared using several methods with the following general formulation:

| Component | Amount (%) |
|---|---|
| Alginic acid | 4.25 |
| Xanthan gum | 3.0 |
| Glycerol | 8.0 |

-continued

| Component | Amount (%) |
| --- | --- |
| Lactic acid | 2.0 |
| Citric acid | 1.0 |
| Potassium bitartrate | 0.4 |
| Benzoic acid | 0.2 |
| Nonoxynol-9 | 0 to 10.0 |
| Distilled water | balance |

Gels were made containing varying levels of nonoxynol-9 (i.e., from 0 to about 10 percent). The pH of the formulations was adjusted to a pH of about 3.5 to about 3.6 with sodium hydroxide. Good quality trapping gels were obtained with this formulation. Moreover, and unlike the formulations of Example 2, these formulations demonstrated good stability for prolonged periods of time even with nonoxynol-9 levels of up to about 5 percent.

As noted above, the trapping gels of this invention are generally prepared using conventional gel preparation techniques. It is important, however, to ensure that the buffering agents are fully solubilized in the final product and that the entrapment of air in the gel is avoided or at least kept to a minimum. This example provides several methods by which the trapping gels of this invention can be made using laboratory scale equipment. Of course, other methods (i.e., different orders of addition of components as well as variation of other variables) can be used so long as the trapping gel produced has similar properties as described in the present specification. The methods described below generally provide equivalent trapping gels.

Method 1.

Using the formulation presented above, benzoic acid (4.0 g) is added to stirred water (950 ml) followed by the addition of sodium hydroxide (150 ml of a 1N solution or any other combination of volume and normality to provide equivalent amounts of sodium hydroxide). Potassium acid tartrate (8.0 g), citric acid monohydrate (20.0 g), and lactic acid (40.0 ml) are added to the mixture; the pH adjusted to about 3.3 to about 3.6 with 1N sodium hydroxide (pH adjustment step 1). Alginic acid (85 g) is added to the stirred solution in small increments to insure a uniform dispersion and avoid air entrapment. Sodium hydroxide (230 ml of a 1N solution or any other combination volume and normality to provide equivalent amounts of sodium hydroxide) is then added to the solution and stirred for 10 minutes. The pH is measured and the pH adjusted to about 3.3 to about 3.6 (using 1N sodium hydroxide if necessary; pH adjustment step 2). Stirring continues until a uniform mixture is obtained.

In a separate container, xanthan gum (60 g) is mixed with glycerin (160 ml) and stirred until uniform and then slowly mixed with the uniform mixture just described. An amount of water equal to 220 ml minus the volume of water used in pH adjustment steps 1 and 2 is then added to the mixture. The volume of added water will, of course, vary depending upon the strength of sodium hydroxide used in pH adjustment steps 1 and 2. The mixture is stirred for short period (about 15 min) and then allowed to stand for a short period of time (about 10 min). Stirring is then continued until a uniform gel consistency is obtained. The pH is checked and should be in the range of about 3.25 to about 3.80, and more preferably in the range of about from 3.37 and 3.52. If necessary, the pH can be adjusted to bring it into the desired range by addition of sodium hydroxide solution.

Method 2.

Using the same formulation, benzoic acid (4.0 g) is dissolved in water (950 ml) with stirring (i.e., magnetic, mechanical, rotatory, vibratory, or ultrasonic stirrer and the like). Without waiting for complete dissolution of benzoic acid, sodium hydroxide (150 ml of a 1N solution or any other combination of volume and normality to provide equivalent amounts of sodium hydroxide) is added and stirring continued. Potassium acid tartrate (8.0 g) is then added to the mixture. The stirring speed or efficiency can be increased to ensure dissolution of the components. Citric acid monohydrate (20.0 g) is then added with stirring. Lactic acid (40.0 ml) is then transferred to the mixture (a small volume of distilled water is used to rinse the transfer vessel) and the pH adjusted to about 3.3 to about 3.6 with 1N sodium hydroxide (pH adjustment step 1). The buffer salts and acids can be dissolved or added in any order. Alginic acid (85 g) is added to the stirred solution in small increments (about one half to one spoonful per addition in batch laboratory scale equipment) to insure that the alginic acid is uniformly dispersed in the mixture without significant entrapment of air. Sodium hydroxide (230 ml of 1N solution or any other combination of volume and normality to provide equivalent amounts of sodium hydroxide) is then added to the solution and stirred for 10 minutes. The pH is measured and the pH adjusted to about 3.3 to about 3.6 (using 1N sodium hydroxide if necessary; pH adjustment step 2). Stirring continues for approximately 30 minutes or for a sufficient period of time to ensure uniform mixing.

In a separate container, xanthan gum (60 g) is mixed with glycerin (160 ml) and stirred until uniform. The uniform solution just prepared is then slowly transferred to the container with xanthan gum and glycerin with continuous stirring. The volumes of 1N sodium hydroxide used in the pH adjusting steps 1 and 2 are added and subtracted from 220 ml. An amount of water equal to 220 ml minus the volume of water used in pH adjustment steps 1 and 2 is then added to the mixture. The volume of added water will, of course, vary depending upon the strength of sodium hydroxide used pH adjustment steps 1 and 2. The mixture is stirred so as to obtain a reasonably uniform mixture without an excessive amount of air entrapment in the thickened preparation. The mixture is allowed to stand for about 10 minutes and then stirred for sufficient time to obtain a uniform gel consistency (normally about 15 minutes). The pH is checked and should be in the range of about 3.25 to about 3.80, and more preferably in the range of about from 3.37 and 3.52. If necessary, the pH can be adjusted to bring it into the desired range by addition of sodium hydroxide solution.

The trapping gels prepared using Methods 1 and 2 had essentially the same properties. For clinical use, the trapping gels should, of course, be analyzed to determine if product specifications for various physico-chemical parameters (e.g., color, consistency, gel separation, odor, final pH (3.37–3.52), buffering capacity, and concentration of any added active ingredient) are achieved. The buffering capacity should be sufficient so that the pH of a mixture of 400 μl 1N NaOH in 40 ml of a 5 percent aqueous solution of the trapping gel is not more than 4.55. Of course, as those skill in the art will realize, some product specifications or parameters (e.g., color or odor) may not significantly impact clinical effectiveness per se but can have a significant on impact consumer acceptance and, thus, the degree to which the product is used and protection is provided.

The active ingredient (i.e., antimicrobial and/or contraceptive agents) can be added at an appropriate stage, depending upon the physico-chemical properties of the material. For example, a surfactant such as Nonoxynol-9, which has a tendency to induce foaming, is preferably incorporated into the xanthan gum and glycerol mixture.

Other antimicrobial and/or contraceptive agents can be incorporated at any time during the preparation of the gel and most preferably before the final consistency is attained so as to avoid entrapment of air in the gel.

EXAMPLE 2

Additional gels were prepared with hydroxyethyl cellulose as a second bio-adhesive agent. The following general formulation was prepared:

| Component | Amount (%) |
|---|---|
| Alginic acid | 3.5 |
| Xanthan gum | 2.0 |
| Hydroxyethyl cellulose | 1.75 |
| Glycerol | 10.0 |
| Lactic acid | 2.0 |
| Citric acid | 1.0 |
| Potassium bitartate | 0.4 |
| Benzoic acid | 0.2 |
| Nonoxynol-9 | 0 to 10.0 |
| Distilled water | balance |

The gel was prepared using same general methods as in Example 1 except that hydroxyethyl cellulose was mixed with the glycerol and xanthan gum mixture.

Trapping gels were made containing varying levels of nonoxynol-9 (i.e., 0 to about 10 percent). The pH of the formulations were adjusted to a pH of about 3.5 to about 3.6 with sodium hydroxide. Formulations prepared with usual levels of nonoxynol-9 (i.e., greater than about 5 percent), however, were not as stable as desired. Stability studies indicated that these nonoxynol-9 formulations tended to separate into a liquid and semisolid phase within about 60 days at about 37 C. Further evaluations indicated that the lack of stability was in large part due to the incompatibility of the hydroxyethyl cellulose and nonoxynol-9. Thus, it is preferred that trapping gels using hydroxyethyl cellulose as one of the bioadhesive agents should contain less than about 5 percent (and more preferably even less) of nonoxynol-9.

EXAMPLE 3

This example illustrates the acid buffering capabilities of the gels of this invention. (Additional, and generally more detailed, studies regarding the acid buffering capabilities of the gels of this invention are included in Example 10 below.) Using the gel as prepared in Example 1, the pH of the gel before and after mixing with various amounts of semen were determined. Semen samples were collected from healthy human volunteers and screened for sperm count, motility, pH, and volume; the initial pH of the semen was about 7.9. The gel was diluted with saline and mixed with semen at the desired ratio of gel to semen. The following results were obtained:

| Dilution of Gel With Saline | pH After Mixing with Semen |
|---|---|
| 1:5 | 3.97 |
| 1:10 | 4.49 |
| 1:20 | 5.66 |

The 1:5 dilution ratio represents about 1 part gel with about 1 part semen; the 1:10 dilution ratio represents about 1 part gel with about 2 parts semen. Since an average ejaculate measures about 1 to about 5 ml and assuming a typical application rate of about 5 ml of the gel, a 1:1 ratio of gel:semen should represent the average dilution that might be expected in most cases. Thus, the present gel has sufficient acid buffering capacity to maintain the pH below 5 even in the presence of higher than normal amounts of ejaculate.

The gel was also diluted with water to about 15 percent and titrated with 1N NaOH. The gel required about 0.5 and 1.5 milliequivalent of NaOH to raise the pH to 4 and 5, respectively. The $pK_a$ value of the preparation was 4.16 as determined from the first derivative plot.

Along with its contraceptive and anti-STD action, gels of the present invention should act to restore and maintain normal vaginal acidity through its buffering action. As shown above, the gel can neutralize up to twice its own volume of semen and maintain the pH below about 4.5. In addition, since the alginic acid is not significantly absorbed (largely because of its high molecular weight) by the body, the buffering capacity of the formulation is expected to be maintained even after the other buffering agents are absorbed.

EXAMPLE 4

This example illustrates the spermicidal activity of the gels of this invention without any added nonoxynol-9. (Additional, and generally more detailed, studies regarding the spermicidal activity of the gels of this invention are included in Example 10 below.) A gel as prepared in Example 1 was used. The spermicidal activity was tested by diluting the gel with physiological saline and mixing with semen in a 5:1 ratio (diluted gel to semen) and microscopically determining the percentage of motile spermatozoa after 30 seconds (Sander Cramer Test). The semen sample had an original volume of about 4.5 ml, a sperm concentration of about $56 \times 10^6$ sperm/ml, and an overall sperm motility of about 55 percent. The following results were obtained:

| Dilution of Gel with Saline | Sperm Motility | Inhibition of Sperm Motility (%) |
|---|---|---|
| 1:5 | 0 | 100 |
| 1:10 | 0 | 100 |
| 1:20 | 20 | 63 |
| 1:40 | 54 | 2 |

Under these conditions, a 1:5 dilution of the gel, when mixed with semen in a 5:1 ratio, represents approximately a 1:1 ratio of undiluted gel with semen; a 1:10 dilution represents approximately a 1:2 ratio of undiluted gel with semen; and a 1:20 ratio represents approximately a 1:4 ratio of undiluted gel with semen. Since an average ejaculate measures about 1 to about 5 ml and assuming a typical application rate of about 5 ml of the gel, a 1:1 ratio of gel:semen should represent the average dilution that might be expected in most cases of sexual intercourse. Thus, the present gel has sufficient spermicidal capacity to inactivate essentially all the spermatozoa even in the presence of higher than normal amounts of ejaculate.

As shown above, the gels of this invention, without a contraceptive agent, are effective spermicides. All the spermatozoa were immediately immobilized when semen was mixed with 10-fold diluted gel (with no nonoxynol-9).

The addition of varying amounts of nonoxynol-9 to the gel enhances its spermicidal properties as illustrated in the following Table I. The experiments were performed exactly as described above for the gel without nonoxynol-9. The semen sample used with the gels containing 0.5 percent or 1.0 percent nonoxynol-9 had a volume of 5.0 ml, a sperm concentration of $70 \times 10^6$ sperm/ml, and an overall sperm motility of 69 percent. The semen sample used for the gel with 2.5 percent nonoxynol-9 had a volume of 4.5 ml, a sperm concentration of $56 \times 10^6$ sperm/ml and an overall sperm motility of 55 percent.

TABLE I

| Dilution of gel | Sperm Motility/Percent Inhibition | | |
|---|---|---|---|
| | Gel with 0.5% N-9 | Gel with 1.0% N-9 | Gel with 2.5% N-9 |
| 1:40 | 0/100% | — | — |
| 1:50 | 2/97% | 0/100% | 0/100% |
| 1:100 | 64/10% | 9/86% | 0/100% |
| 1:200 | — | 55/20% | 12/78% |
| 1:400 | — | — | 55/0% |

Thus, it appears that reduced levels of nonoxynol-9 can be used in the gels of this invention while retaining spermicidal efficacy in vivo. Lower nonoxynol-9 concentrations would decrease the possibility of vaginal irritation due to this detergent.

EXAMPLE 5

Rabbit vaginal irritation testing using standard testing protocol was performed on the trapping gel from Example 1 containing 0, 2.5, and 5 percent nonoxynol-9. Rabbits were dosed vaginally with a test substance/formulation (1 ml dose) for ten consecutive days followed by excision of the vaginal tissue, fixation in buffered formalin, and histological examination of three regions of the abdominal vagina. The fixed tissues were trimmed, blocked, mounted in paraffin blocks, sectioned, and stained with hematoxylin and eosin. Sections were obtained from the anterior abdominal, mid-abdominal, and posterior abdominal vagina. Histological scoring was based upon alterations in the epithelium, vascular congestion, leukocyte infiltration, and edema. Total scoring is based upon a maximum score of four for each criterion with a maximum of 16. A score of 4 or less are is considered minimal irritation, 5 to 8 mild irritation, 9 to 11 moderate irritation, and 12–16 marked irritation. Traditionally, the conclusions are categorized as acceptable for clinical use with a score of 0–8, borderline for a score of 9–11 and unacceptable for a total score of 12 and above.

All the animals tolerated the dosing well and there were no pharmacotoxic signs observed in any of the groups. Test article was observed in the vaginal vault during gross necropsy in several of the animals treated with the trapping gel preparations. No gross changes in the vaginas of any treated animals were observed. The histopathology scores are as follows:

TABLE II

| Sample | Mean Score |
|---|---|
| Untreated (n = 6) | 0.8 |
| Sham Saline (n = 6) | 3.7 |
| Trapping Gel (0% N-9) (n = 10) | 5.3 |
| Trapping Gel (2.5% N-9) (n = 10) | 6.8 |
| Trapping Gel (5% N-9) (n = 10) | 8.6 |

Trapping gels with either no added nonoxynol-9 or 2.5 percent nonoxynol-9 exhibited mild irritation whereas the trapping gel with 5 percent nonoxynol-9 exhibited moderate irritation. All three formulations of the trapping gels were considered acceptable for clinical evaluation.

EXAMPLE 6

This example illustrates the anti-herpes activity of the gels (with and without nonoxynol-9 (N-9)) of this invention. Gels as prepared in Example 1 were used. Both in vitro and in vivo studies were carried out. The following formulations were evaluated for anti-herpes activity:

(1) Inventive gel without nonoxynol-9
(2) Inventive gel with 5 percent nonoxynol-9
(3) Inventive gel with 2.5 percent nonoxynol-9
(4) K-Y jelly (Advanced Care Products) (control 1)
(5) K-Y jelly with 2.2 percent nonoxynol-9 (Advanced Care Products; K-Y Plus™) (control 2).
(6) Phosphate buffered saline (PBS) (control 3).

In Vitro Studies.

Both inventive gel with and without added nonoxynol-9 were evaluated for in vitro activity against herpes virus by Dr. B. Herold, Mount Sinai School of Medicine, New York, N.Y. HSV-2 strain 186 was prepared by culture in low-passage primary rabbit kidney (RK) cells. Plaque reduction assays were conducted as described by Herold et al., *Antimicrobial Agents Chemother.*, 43, 745–751 (1999). The results are shown in Table III.

TABLE III

| Inventive Gel | | | Inventive Gel with 2.5% nonoxynol-9 | | |
|---|---|---|---|---|---|
| mg/ml | pfu/well | inhibition (%) | mg/ml | pfu/well | inhibition (%) |
| 40 | hostcell death | — | 40 | hostcell death | — |
| 4 | 12 | 72 | 4 | hostcell death | — |
| 0.4 | 24 | 44 | 0.4 | 17 | 60 |
| 0.04 | 42 | 2 | 0.04 | 32 | 26 |

A control (medium only) obtained an average of 43 pfu/well and a range of 32 to 53 pfu/well.

The inventive gel is an effective inhibitor of herpes in vitro. The addition of nonoxynol-9 to the inventive gel appears to increase the anti-herpes effect; the effect due to the added nonoxynol-9 appears, however, to be relatively small. As expected, the addition of nonoxynol-9 increases host cell toxicity.

In Vivo Studies.

Both inventive gel with and without added nonoxynol-9 were evaluated for in vivo activity against the herpes virus using mice. The results were presented by V. Pilipenko, N. Bourne, L. J. D. Zaneveld, S. Garg, D. P. Wailer, and L. R. Stanberry at the Thirteenth Meeting of the International Society for Sexually Transmitted Diseases Research, Denver, Colo., on Jul. 11–14, 1999. The HSV-2 strain 186 was used as prepared above.

Female Swiss Webster mice weighing 18–21 g (Harlan, Indianapolis, Ind.) were administered 0.1 ml of a suspension containing 3 mg of medroxyprogesterone acetate (Upjohn Pharmacia, Kalamazoo, Minn.) by subcutaneous injection in the shoulder region 7 days prior to virus challenge and then the day before virus challenge, to increase susceptibility to vaginal HSV infection. On the day of viral challenge, animals were anesthetized by intra peritoneal injection of 0.25 ml of a solution containing 6.5 mg/ml sodium pentobarbitol. The vaginal vault was swabbed twice, first with a moistened type 1 calcium alginate-tipped swab (Fisher Scientific, Pittsburgh, Pa.) and then with a dry swab. Twenty seconds later, the animals were challenged intravaginally by instillation of 15 μl of a suspension containing 4.0 $\log_{10}$ pfu of HSV-2 strain 186.

Vaginal swab samples were collected from all animals two days after inoculation and stored frozen (−80 C.) until assayed for the presence of virus by culture on susceptible RK cell monolayers. Mice were evaluated daily, up to day 21 after inoculation, for evidence of symptomatic infection that included hair loss and erythema around the perineum, chronic urinary incontinence, hind-limb paralysis, and mortality. For the purpose of these studies, animals that did not develop symptoms were defined as infected if virus was isolated from vaginal swab samples collected on day 2 after inoculation. Incidence data were compared by Fisher's exact test. All comparisons were two-tailed.

The protective efficacy of non-formulated nonoxynol-9 (i.e., in normal saline only) at different concentrations against genital herpes infection in the mouse model was determined. As shown in Table IV, animals treated 20 seconds prior to virus challenge with a concentration of at least 50 percent nonoxynol-9 obtained significant protection against both disease and infection compared to PBS treated control animals ($p<0.001$ each); of course, such high levels of nonoxynol-9 would not be practical because of the high irritation factor. In contrast, animals treated with a 5 percent nonoxynol-9 solution (i.e., a concentration similar to that in many commercial contraceptive formulations) became infected, although there was some reduction in the number of animals that developed symptomatic disease ($p<0.05$).

TABLE IV

Effect of N-9 Controls in PBS Against Genital Herpes Simplex Virus Type 2 in Mice.

| | Time Administered | Number | Protected Against Disease | | Protected Against Infection[b] | |
|---|---|---|---|---|---|---|
| | (sec.)[a] | Inoculated | Number | % | Number | % |
| PBS | 20 | 15 | 0 | 0 | 0 | 0 |
| N-9 (100%) | 20 | 15 | 15 | 100[c] | 14 | 93[c] |
| N-9 (50%) | 20 | 15 | 15 | 100[c] | 14 | 93[c] |
| N-9 (5%) | 20 | 15 | 6 | 40[d] | 2 | 13 |

[a]Time relative to virus inoculation
[b]Animals that did not develop symptoms were defined as infected if virus was isolated from vaginal swabs collected on day 2 after inoculation
[c]$p < 0.001$ vs. PBS, Fishers exact test
[d]$p < 0.05$ vs. PBS, Fishers exact test Similar studies were carried out using commercially available spermicide preparations containing nonoxynol-9 at concentrations varying between about 2.2 to about 3.5 percent. The commercially available spermicide preparations included: K-Y Plus™ (2.2 percent nonoxynol-9; Ortho-McNeil Pharmaceutical Corp., Raritan, N.J.); Encare™ (3 percent nonoxynol-9; Thompson Medical Co, West Palm Beach, Fla.); Conceptrol™ (5 percent nonoxynol-9; Ortho-McNeil Pharmaceutical Corp); Gynol II™ (2 percent nonoxynol-9; Ortho-McNeil Pharmaceutical Corp); and Advantage™ (3.5 percent nonoxynol-9; Columbia Laboratories; now available under the Advantage-S™ tradename). As shown in Table V, the protection against disease and infection was only modest and was comparable with that seen in the previous study with unformulated 5 percent nonoxynol-9.

TABLE V

Effect of Conventional Nonoxynol-9 Formulations Against Genital Herpes Simplex Virus Type 2 in Mice.

| | Time Administered | Number | Protected Against Disease | | Protected Against Infection[b] | |
|---|---|---|---|---|---|---|
| | (sec.)[a] | Inoculated | Number | % | Number | % |
| PBS | 20 | 47 | 1 | 2 | 0 | 0 |
| K-Y Plus ™ (2.2% N-9) | 20 | 15 | 2 | 13 | 1 | 7 |
| Encare ™ (3% N-9) | 20 | 15 | 6 | 40 | 4 | 27 |
| Gynol II ™ (2% N-9) | 20 | 16 | 3 | 19 | 0 | 0 |
| Conceptrol ™ (4% N-9) | 20 | 15 | 6 | 40 | 4 | 25 |
| Advantage ™ (3.5% N-9) | 20 | 16 | 8 | 50 | 8 | 50 |

[a]Time relative to virus inoculation
[b]Animals that did not develop symptoms were defined as infected if virus was isolated from vaginal swabs collected on day 2 after inoculation A series of similar experiments were also carried out using the invention gels of this invention. The results are shown in Tables VI and VII.

TABLE VI

Effect of Inventive Gels (with and without Nonoxynol-9) and Conventional Nonoxynol-9 Formulations Against Genital Herpes Simplex Virus Type 2 in Mice.

| | Time Administered | Number | Protected Against Disease | | Protected Against Infection[b] | |
|---|---|---|---|---|---|---|
| | (sec.)[a] | Inoculated | Number | % | Number | % |
| PBS | 20 | 15 | 0 | 0 | 0 | 0 |
| K-Y Jelly ™ | 20 | 15 | 0 | 0 | 0 | 0 |
| K-Y Plus ™ (2.2% N-9) | 20 | 15 | 3 | 20 | 0 | 0 |
| Inventive Gel (no added N-9) | 20 | 15 | 4 | 27 | 1 | 7 |
| Inventive Gel + 2.5% N-9 | 20 | 15 | 11 | 73 | 5[c,e] | 33[d] |

[a]Time relative to virus inoculation
[b]Animals that did not develop symptoms were defined as infected if virus was isolated from vaginal swabs collected on day 2 after inoculation
[c]$p < 0.001$ vs. PBS, Fishers exact test
[d]$p < 0.05$ vs. PBS, Fishers exact test
[e]$p < 0.01$ vs. KY + N9, Fishers exact test

TABLE VII

Effect of Inventive Gels (with and without Nonoxynol-9) and Conventional Nonoxynol-9 Formulations Against Genital Herpes Simplex Virus Type 2 in Mice.

| | Time Administered[a] | Number Inoculated | Protected Against Disease | | Protected Against Infection[b] | |
|---|---|---|---|---|---|---|
| | | | Number | % | Number | % |
| PBS | 20 sec | 15 | 2 | 13 | 0 | 0 |
| Inventive Gel (no added N-9) | 20 sec | 16 | 8 | 50 | 6 | 38 |

TABLE VII-continued

Effect of Inventive Gels (with and without Nonoxynol-9) and Conventional Nonoxynol-9 Formulations Against Genital Herpes Simplex Virus Type 2 in Mice.

| Time Administered[a] | Number Inoculated | Protected Against Disease Number | % | Protected Against Infection[b] Number | % |
|---|---|---|---|---|---|
| Inventive Gel + 5% N-9 20 sec | 16 | 15 | 94[c] | 15 | 94[c] |
| Inventive Gel + 5% N-9 30 min | 16 | 12 | 75[c] | 6 | 38 |

[a]Time relative to virus inoculation
[b]Animals that did not develop symptoms were defined as infected if virus was isolated from vaginal swabs collected on day 2 after inoculation
[c]$p < 0.001$ vs. PBS, Fishers exact test Tables VI and VII illustrate some of the characteristics of the inventive gel which makes it especially attractive as an anti-STD formulation for vaginal use. For example, the protection against disease and infection using the inventive gel alone (i.e., no nonoxynol-9) was better than that obtained with conventional contraceptives (i.e., K-Y Plus™ or Gynol II™ M). Furthermore, the inventive trapping gel alone was as active or more active than Conceptrol™ or the Advantage™ product. Thus, the trapping gel alone is as active as presently marketed preparations even if they are bioadhesive and contain from 2.2 to 3.5 percent nonoxynol-9.

As shown in Table VII, the nonoxynol-9 level of the inventive gel was raised to about 5 percent. These formulations provided good protection against both disease and infection when animals received the virus challenge soon after treatment. The formulations of this invention provided significant protection against disease even when the virus challenge was delayed thirty minutes. As those skilled in the art will realize, an effective contraceptive or anti-STD formulation should provide such long term protection.

EXAMPLE 7

This example illustrates the anti-*Chlamydia trachomatis* activity of the gels (with and without nonoxynol-9 (N-9)) of this invention. The MoPn biovar of *C.trachomatis* strain Nigg II (VR-123; American Type Culture Collection, Manassas, Va.) was used in all studies. Stock cultures were propagated in McCoy cells by a modification of the procedure of Cooper et al. (Gen. Microbio. 1990; 136: 1109–1115). Briefly, cycloheximide-treated McCoy cells in 175 cm² flasks were detached 72 hours after infection by scraping and sonicated to lyse the host cells. Chlamydial elementary bodies were pelleted and resuspended in 0.2 M sucrose/0.02 M phosphate buffer (Bird et al., Public Health Service, Center for Disease Control, 1981) and frozen (−80 C.). Titers of *C. trachomatis* stock cultures were determined by inoculating McCoy cells in 48-well tissue culture plates with 0.1 ml of 10-fold dilutions prepared from the frozen sample. After incubation for 48 hours, the cultures were fixed, stained, and the number of chlamydial inclusion-forming units enumerated with fluorescein-conjugated antibody to the chlamydial antigen (Bartels, Issaquah, Wash.).

The anti-*C. trachomatis* activity of both the inventive gels and several commercial vagina products were evaluated. Female Swiss Webster mice weighing 18–21 g (Harlan, Indianapolis, Ind.) were administered 0.1 ml of a suspension containing 3 mg of medroxyprogesterone acetate (Upjohn Pharmacia, Kalamazoo, Mich.) by subcutaneous injection in the shoulder region 7 days prior to virus challenge and then the day before the virus challenge, to increase susceptibility to vaginal HSV infection. On the day of viral challenge, animals were anesthetized by intra peritoneal injection of 0.25 ml of a solution containing 6.5 mg/ml sodium pentobarbitol. The vaginal vault was swabbed twice, first with a moistened type 1 calcium alginate-tipped swab (Fisher Scientific, Pittsburgh, Pa.) and then with a dry swab. The anesthetized animals were then administered 15 μl of the test formulation prior to pathogen challenge.

Animals were inoculated by instillation of 15 μl of a suspension containing 4.0 $\log_{10}$ IFU of *C. trachomatis* MoPn. Vaginal swab samples were collected from all animals on days 3 and 6 post inoculation and stored frozen (−70 C.) until assayed for the presence of *C. trachomatis* on McCoy cell monolayers. Animals were defined as having lower genital tract infection if *C. trachomatis* was isolated from either sample. To determine the incidence of upper genital tract infection, animals were sacrificed on day 10 PI and the oviducts and ovaries harvested. The tissues were cut into 2–3 mm² sections and stored frozen (−70° C.). Samples were thawed, sonicated, and clarified by centrifugation prior to culture on McCoy cell monolayers. In some cases, animals were sacrificed on day 35 post inoculation and the upper genital tract examined for pathologic evidence of upper genital tract infection (i.e., hydrosalpinx). The results for the commercial vaginal products and the inventive gels are shown in Tables VIII and IX, respectively.

TABLE VIII

| | Lower Genital Tract Protected against infection/inoculated[a] | Upper Genital Tract Protected against infection/inoculated[b] |
|---|---|---|
| PSB | 2/29(7%) | 4/29(14%) |
| Gynol II ™ (2% N-9) | 6/16 (38%)[c] | 6/16 (38%) |
| K-Y Plus ™ (2.2% N-9) | 0/16 (0%) | 1/16 (6%) |
| Advantage-S ™ (3.5% N-9) | 3/16 (19%) | 3/16 (19%) |
| Conceptrol ™ (4% N-9) | 0/16 (0%) | 0/16 (0%) |

[a]Animals were defined as infected if *C. trachomatis* was isolated by culture from swab samples collected on either day 3 or day 6 post inoculation.
[b]Samples were collected on day 10 post inoculation.
[c]$p < 0.05$ vs. PBS

TABLE IX

| | Lower Genital Tract | Upper Genital Tract | |
|---|---|---|---|
| | Protected against infection/inoculated[a] | Protected against infection/inoculated[b] | Protected against hydrosalpinx/inoculated[c] |
| PSB | 1/16 (6%) | 0/8 (0%) | 2/8 (25%) |
| Inventive Gel (no added N-9) | 13/16 (81%)[d] | 8/8 (100%)[e] | 7/8 (88%)[f] |
| Inventive Gel with 5% N-9 | 10/16 (62%)[e] | 4/8 (%)[f] | 8/8 (100%)[e] |

[a]Animals were defined as infected if *C. trachomatis* was isolated by culture from swab samples collected on day 3 or day 6 post challenge.
[b]Samples were collected on day 10 post-challenge
[c]Mice were considered to have developed hydrosalpinx if any hydrovesicle was visible on day 35
[d]$p < 0.001$ vs. PBS
[e]$p < 0.01$ vs. PBS
[f]$p < 0.05$ vs. PBS The inventive gel, with or without nonoxynol-9, is highly effective in preventing chlamydia infection in mice. Moreover, the inventive gel is more effective than any of the commercial products evaluated in protecting against chlamydia infection in mice.

EXAMPLE 8

Clinical trials of the inventive formulations of this invention have also been conducted by Dr. Eliana Amaral and Dr. Anibal Faundes, University of Campinas, Campinas, Brazil, in collaboration with the inventors. These trials were designed to determine vaginal tolerance to the inventive gel with and without nonoxynol-9. The inventive gel used was similar to that prepared in Example 1. Three formulations of the inventive gel were used: (1) inventive gel with no added nonoxynol-9; (2) inventive gel with 2.5 percent nonoxynol-9; and (3) inventive gel with 5.0 percent nonoxynol-9.

A randomized, double blinded, phase I clinical trial was conducted using 18 volunteers (six volunteers treated with each of the three formulations). Women included in the study were 20–49 years of age, sexually active, with regular menstrual cycles, not at risk for pregnancy (i.e., using tubal ligation, IUD, partner vasectomy), and having good genital health as evaluated by clinical history, physical examination, and STD-screening tests. The volunteers were asked to abstain from intercourse 48 hours before admission into the study and during the study. They also agreed to visit the clinic for follow up evaluations on the second and seventh days after the initial visit and start of the protocol. Women with a history of an STD in the last 12 months, who had used any vaginal product within 7 days before admission, or with known allergy to nonoxynol-9 were excluded.

Volunteers were also required to abstain from use of other intravaginal products, including spermicides, tampons, and douches, for the duration of the study (unless prescribed by the investigator). They were also asked to abstain from intercourse for at least two days before admission in the study and while using the test products with the purpose of avoiding the influence of semen and possible trauma during vaginal intercourse.

The volunteers were seen in four different visits: screening visit, first visit (day 1), second visit (day 2) and third visit (day 7). They were given an appointment for screening and admission during the follicular phase of their menstrual cycle (days 6–9). At the screening visit, they were provided with a description of the study's objectives; clinical histories, physical exams, pregnancy tests, and check lists with the inclusion and exclusion criteria were given. The informed consent form was read and signed. Leukocyte counts in endocervical samples were carried out at this screening visit. Treatment for endocervicitis was prescribed if 30 or more leukocytes per high power field was noted, edema/friability of the cervix was present, or a positive N. gonorrhea culture was found. Whiff test, vaginal pH, Gram stained and fresh mount were performed to screen for vaginal infections. The finding of ectropium or the presence of T vaginalis, hyphas, positive Whiff test, pH>4.7, or clue cells postponed admission until a negative exam was obtained.

In the following three visits, irritation (i.e., vulvar, vaginal, and cervical) was assessed through a colposcopic exam following a WHO protocol for evaluation of new vaginal products (World Health Organization, Global Programme on AIDS (WHO), "Manual for the Standardization of Colposcopy for the Evaluation of Vaginally Administered Products," VMO/GPA/CRD/95, 10 Geneva 1995, 15 p.). Ulceration, de-epithelialization, abrasion, and erythema were considered signs of irritation. Findings were recorded and photographic documentation of the vulva, cervix, and right lateral fornix were obtained. To clean the vaginal fornix and cervix, a saline moistened swab was gently applied before WHO standardized colposcopy.

The first visit (day 1) was set at the next follicular phase (cycle days 6–9). After baseline colposcopy, five ml of the randomly assigned inventive gel (0 percent, 2.5 percent, or 5 percent of Nonoxynol-9) was applied by the investigator. Volunteers were instructed to return the next morning in order to evaluate the possible short-term effects of the product on the lower genital tract. During the second visit (day 2), after colposcopic procedures, the volunteers were instructed to self-insert five ml of the gel every night immediately before sleeping for five additional nights, while in recumbent position. They also received a form to make notes of symptoms and time of self-application of the gel and were instructed to contact the investigators if they had questions or any significant discomfort. They were scheduled to return the morning following completion of the five-day treatment period. During the third and last visit (day 7), final colposcopic evaluation was performed. At this visit, a questionnaire about symptoms of observations (e.g., sensation of "lubrication" or leakage, and other related effects) during use of the gel was administered. The patients' forms containing their records of any adverse experience during the six days period were collected at this visit.

In two cases (#2 and #3) the protocol was broken with regard to the first day of application of gel by the volunteer due to difficulties in scheduling a visit. These patients, therefore, did not use the inventive gel for one day between the initial application by the researcher at the first visit and the beginning of the self-administered five applications. Additionally, treatment of two other volunteers (cases #5 and #6) was initiated on the 10th day of the cycle (instead of from the 6th to the 9th day). Volunteers had the freedom to drop out of the study if they experienced any bleeding, unacceptable pain, irritation, or burning, or for any other reason. None of the volunteers left the study and all volunteers completed the study.

None of the volunteers had complaints at the second visit. During the first few days of self-application, four subjects registered complaints (three reported burning and itching and one reported "tenderness" of the vagina). All of these subjects were using inventive gel formulations which contained nonoxynol-9. Only one of these four subjects considered the symptoms to be "severe"; nonetheless, this subject completed the trial and reported that the symptoms had disappeared by the last visit. These same four subjects showed vulvar and cervical erythema at the final colposcopy examination. The volunteer with the most severe symptoms had a moderate erythema of the cervix and mild erythema of the vulva, but her vaginal content was yellowish (pH of 7.0). Eleven of the volunteers reported some leakage of the gel; only four considered it as "annoying or disgusting." Two of the six users of the inventive gel (0 percent nonoxynol-9) noted some leakage "at the time of going to the toilet."

On colposcopy, isolated petechiae were observed in the cervix or vagina of nine out of the 18 volunteers during the first visit (i.e., before the application of any gel). These petechiae were attributed to the trauma caused by the insertion of the speculum or by a gentle cleansing with the moistened swab. During the second visit (i.e., after one day of gel usage), seven subjects showed erythema: vulva (2), cervix (3), and vagina (4). Six of these subjects were using the nonoxynol-9-containing gels (2.5 or 5.0 percent); only one was using the inventive gel without N-9. Two of these subjects had erythema in more than one location.

At the third visit (i.e., after self-application of the gel for five consecutive nights), no erythema or abrasion was found among users of inventive gel without nonoxynol-9. However, erythema of the cervix was observed in all subjects using the inventive gel containing nonoxynol-9. Out of the twelve subjects using the inventive gel with nonoxynol-9, ten presented erythema which was intense and generalized. For the other two nonoxynol-9 users, gel adhered to the cervix and localized erythema could be observed at the base of the area when the film was withdrawn. Abrasion caused by gentle cleansing of the cervix or vagina with moistened swab, occurred in nine of the ten subjects with generalized erythema. Four of these ten volunteers also had intense erythema of the vagina and seven had vulvar erythema. Ulcers, exulcerations, or de-epithelialization (i.e., more severe signs of irritation) were not observed in any of the subjects regardless whether the inventive gel contained nonoxynol-9 or not.

An adhesive layer of inventive gel over the cervix was observed with the colposcope in three subjects during both the second and third visits. An adhesive layer of inventive gel over the cervix was observed in 83 percent of the subjects at the third visit (about 12 hours after the last application of the gel). For ten of the volunteers having an adhesive layer over the cervix, a layer of inventive gel was also observed over the vagina. Vaginal washing with saline was insufficient to remove the film. The three remaining cases, all using the gel without nonoxynol-9, did not show adherence of the gel to the cervix or the vagina.

The summary of the clinical results are provided in Table X.

This clinical study indicates the absence of any vaginal and cervical irritation when the inventive gel is used alone (i.e., without nonoxynol-9) and is applied for six consecutive days. The inventive gel containing 2.5 or 5.0 percent nonoxynol-9 did, however, produce erythema but no serious vaginal irritation. This erythema was not sufficient to cause any of the volunteers to terminate the protocol. The erythema was transient and disappeared within 1 or 2 days after cessation of treatment. Since the trapping gel has antimicrobial and contraceptive properties of its own, it is expected that the levels of nonoxynol-9 can be reduced further, thereby significantly decreasing or eliminating the erythema caused by gel containing nonoxynol-9 while maintaining high anti-STD and contraceptive activities. Moreover, women who are less sensitive to nonoxynol-9 may obtain benefit from the invention gel even with higher levels of nonoxynol-9 used in the clinical trials.

EXAMPLE 9

The ability of various vaginal anaerobes and other vaginal organisms to survive in a mixture of the composition of this invention and a brucella broth at a pH of less than about 4 was evaluated. One part of the inventive composition of Example 1 (with no added nonoxynol-9; pH about 3.55) was mixed with one part brucella broth; the blend had a pH of about 3.48. The test samples were allowed to sit under anaerobic conditions for at least two hours before testing. Inoculums of about $5 \times 10^7$ organisms/ml of various organisms were evaluated in the test samples. Samples were subcultured every hour over a 24 hour period using blood agar under a 5 percent $CO_2$ atmosphere in order to determine how long each microorganism survived. The microbes in Table XI survived one hour or less.

TABLE X

|  | Day 1 | | | Day 2 | | | Day 3 | | |
| --- | --- | --- | --- | --- | --- | --- | --- | --- | --- |
|  | 0% N-9 | 2.5% N-9 | 5% N-9 | 0% N-9 | 2.5% N-9 | 5% N-9 | 0% N-9 | 2.5% N-9 | 5% N-9 |
| Erythema, vulva | 0 | 0 | 0 | 0 | 2 | 0 | 0 | 3 | 4 |
| Erythema, cervix | 0 | 0 | 0 | 0 | 0 | 3 | 0 | 6 | 6 |
| Erythema, vagina | 0 | 0 | 0 | 1 | 2 | 1 | 0 | 2 | 3 |
| Abrasion, vulva* | 0 | 0 | 0 | 0 | 0 | 0 | 0 | 0 | 0 |
| Abrasion, cervix* | 0 | 0 | 0 | 0 | 0 | 0 | 0 | 5 | 4 |
| Abrasion, vagina* | 0 | 0 | 0 | 0 | 0 | 0 | 0 | 2 | 3 |

*Abrasion due to swabbing vagina.

TABLE XI

| Sample Number | Microorganism |
|---|---|
| 11423 | F. gonidiaformans |
| 11653 | F. gonidiaformans |
| 10481 | F. nucleatum |
| 11518 | F. nucleatum |
| 9052 | Prev. melaninogen. |
| 11142 | Prev. intermedia |
| 11168 | Prev. intermedia |
| 11697 | Prev. bivia |
| 11683 | Prev. bivia |
| 11579 | Prev. disiens |
| 11698 | Prev. disiens |
| 11690 | Porph. asacch. |
| 11656 | Porph. asacch. |
| 11425 | Porph. levii |
| 11601 | Porph. levii |
| 11598 | Ps. magnus |
| 11658 | Ps. magnus |
| 11253 | Ps. tetradius |
| 11287 | Ps. tetradius |
| 11587 | Ps. asacch. |
| 11607 | Ps. asacch. |
| 9420 | Eubact. lentum |
| 11700 | Eubact. lentum |
| P-53b | Pseudo. aeruginosa |
| P-68a | Pseudo. aeruginosa |
| P-41b | Strep. agalactiae |
| P-109a | Strep. agalactiae |
| 11262 | Gardnerella vaginalis |
| P-51a | Gardnerella vaginalis |

Thus, it appears that the inventive gel has a broad spectrum inhibitory effect on vaginitis- and/or bacterial vaginosis-causing organisms.

EXAMPLE 10

This example provides further data regarding the protective efficacy and other properties of the trapping gels of this invention. Comparisons to various commercial vaginal compositions is also provided. The trappling gel of Example 1 was packaged in 20 gram plastic tubes with screw-caps. The acid-buffering activity of the inventive trapping gel was compared to those of the marketed, vaginal acid-buffering gel, Aci-Jel™ (Ortho-McNeil Pharmaceutical, Raritan, N.J.). The bioadhesive and viscosity-retaining properties of inventive trapping gel were compared to commercial gels including Conceptrol™ (Advanced Care Products, Raritan, N.J.; a commonly used marketed vaginal contraceptive), Advantage S™ (Columbia Laboratories, Aventura, Fla.; a vaginal contraceptive gel claiming to have bioadhesive properties), Replens gel (Parke-Davis, Morris Plains, N.J.; a bioadhesive vaginal moisturizer effective for several days), K-Y Jelly™ (Advanced Care Products; Raritan, N.J.; a frequently used vaginal lubricant), and Aci-Jel™. The marketed products were purchased from a local retail pharmacy.

Semen was collected by self masturbation from five healthy volunteers after obtaining Investigational Review Board (IRB) approval and consent from the volunteers. The average volume of the semen samples was 2.3±0.45 ml, the average sperm concentration was 74×10$^6$ cells/ ml (90 percent confidence limits: 46 to 120×10$^6$ cells/ml), and the average initial percentage of motile spermatozoa was 62 percent (range of 58 to 67 percent).

Acid Buffering Capacity.

Acid buffering capacity was determined by titration with NaOH. One gram of each gel was diluted to 10 ml with 0.9 percent NaCl ("normal" saline) (1:10 w/v). Sodium hydroxide (1.0 N) was added in 20 ml increments under constant stirring. The pH was measured 30 seconds after each addition with a standard combination electrode. Stirring was stopped during pH measurements. This procedure was repeated until the pH rose above 7.0. The titrations were performed in triplicate for each gel. Titration curves were best fitted to the data with TableCurve 2D software (SPSS Software, Chicago, Ill.). These curves were used to calculate the amount of NaOH required to bring the pH of each gel solution to 5.0 (a measure of the buffering capacity of the gel and generally considered the maximal desirable vaginal pH). First derivative values for the curves from X=0 (no NaOH added; the initial pH) to X=mequivalents NaOH required to titrate the gel solution to pH 7.0 were calculated for each curve. First derivative values were also estimated directly from the data with spline interpolation (StatMost statistical software, DataMost Corporation, Sandy, Utah). Minima that were in common for both estimations of the first derivatives of the titrations were used to estimate the apparent $pK_a$ values at or below pH 7.

Relevant buffering capacity of the gels was considered as the amount of NaOH required to bring the pH of the gel from its initial value to 5.0. The inventive trapping gel had much higher acid-buffering capacity than Aci-Jel™. About 0.320 meq NaOH was required to increase the pH of 1 gram of the inventive trapping gel from its initial pH of 3.52 to 5.0; in contrast, about 0.076 meq was required for Aci-Jel™ to raise the pH from its initial value of 4.07 to 5.0. This is consistent with the lower apparent $pK_a$ values obtained for inventive trapping gel (i.e., 3.7, 4.0, and 4.7) as compared to Aci-Jel™ (i.e., 4.4 and 5.0).

The physiologically relevant buffering activity of the gels was estimated by determining the pH after direct addition of whole human semen (pH of about 7.2 to about 8.0) to the undiluted gels in varying proportions (generally ratios of about 1:1 to about 1:9). The pH was measured with a Ross-type spear tipped combination pH electrode. The following results were obtained.

TABLE XII

| Ratio of Gel to Semen | Average pH | |
|---|---|---|
| | Inventive Gel | Aci-Jel ™ |
| Gel only | 3.45 | 4.05 |
| 1:1 | 3.97 | 5.14 |
| 1:2 | 4.45 | 5.79 |
| 1:4 | 5.18 | 6.57 |
| 1:9 | 6.48 | not determined |
| Semen only | 7.64 | |

Confirming the titration measurements, the inventive gel acidified the ejaculate more effectively than Aci-Jel™. For instance, when 1 part gel was mixed with 2 parts semen, the pH remained below 4.5 with the inventive gel but was almost 6.0 with Aci-Jel™. Curves were fit to the data with TableCurve software (SPSS Statistical Software, Chicago, Ill.). The calculated gel:semen ratio to produce a pH of 5.0 is 1:3.4 (22.9 percent gel in gel/semen mixture) for the inventive gel and 1:0.9 (52.5 percent gel in gel/semen mixture) for Aci-Jel™. The calculated pH values from these curves of 100 percent inventive gel and Aci-Jel are 3.53 and 4.08 respectively. These values are in good agreement with the direct pH measurements reported above.

Bioadhesion.

Bioadhesive strength of the inventive gel and other vaginal gel formulations were measured using horizontal and vertical bioadhesion test assemblies (Garg et al., "Rationalization of Selection of Polymers in the Development of Vaginal Formulations in Terms of Their Bioadhesion and Retention Properties," in *Conference Abstracts of Microbicides* 2000, March 13–16, Washington, D.C., p.41) based on the principle of measuring tensile strength (measured using the horizontal test assembly) and shear stress (measured using the vertical test assembly) required to break the adhesive bond between a model membrane and test formulation. Cellophane treated with simulated vaginal fluid (SVF; Owen et al., "A Vaginal Fluid Simulant," *Contraception,* 1999; 59: 91–5) and isolated sheep vaginal mucosa (obtained from a slaughter house) were used as membranes. For measuring bioadhesive strength, 0.5 gm of gel was mixed with 0.25 ml SVF and applied between the membranes over an area of about 12 $cm^2$. The membranes were kept in contact with the gel for 5 minutes. In the horizontal assembly, gel contact with the membranes was established by keeping a weight (10 gm) on the upper support. Before measurement, this weight was removed. In the vertical assembly, a screw was used to maintain gel contact, and removed before measurement. The bioadhesive strength was taken as the force required to separate the two membranes.

Generally, the bioadhesive strength of the inventive gel was greater than any of the marketed products. The results are shown in the following tables.

TABLE XIII

Bioadhesive strengths of vaginal formulations using cellophane membrane

| Formulation | Bioadhesive Strength (dynes/$cm^2$; n = 6) | |
|---|---|---|
| | Horizontal Assembly | Vertical Assembly |
| Inventive gel | 1223 | 774 |
| Aci-Jel ™ | 904 | 471 |
| Advantage S ™ | 441 | 412 |
| Conceptrol ™ | 944 | 410 |
| K-Y Jelly ™ | 913 | 375 |
| Replens ™ | 717 | 328 |

TABLE XIV

Bioadhesive strengths of vaginal formulations using sheep vaginal mucosa membrane

| Formulation | Bioadhesive Strength (dynes/$cm^2$; n = 6) | |
|---|---|---|
| | Horizontal Assembly | Vertical Assembly |
| Inventive gel | 1191 | 833 |
| Aci-Jel ™ | 1143 | 511 |
| Advantage S ™ | 363 | 360 |
| Conceptrol ™ | 641 | 423 |
| K-Y Jelly ™ | 907 | 390 |
| Replens ™ | 1228 | 676 |

In the horizontal assembly, using the cellophane membrane, the bioadhesive strength of inventive gel was about 1.3, 2.8, 1.3, 1.3, and 1.7 fold higher, respectively, than Aci-Jell™, Advantage S™, Conceptrol™, K-Y Jelly™, and Replens™. Using sheep vaginal mucosa membrane in the same assembly, the inventive gel's bioadhesive strength was about 3.3, 1.9, and 1.3 fold greater than, respectively, Advantage S™, Conceptrol™, and K-Y Jelly™ but essentially identical to that of Aci-Jel™ and Replens™. In the vertical assembly using cellophane membrane, the inventive gel was about 1.6, 1.9, 1.9, 2.1, and 2.4 times more bioadhesive than Aci-Jel™, Advantage S™, Conceptrol™, K-Y Jelly™, and Replens™, respectively, and, with sheep vagina mucosa membrane, about 1.6, 2.3, 2.0, 2.1 and 1.2 greater, respectively. In general, the two types of membranes produced similar results with all formulations except Aci-Jel™ and Replens™, which tended to be more bioadhesive towards the sheep vagina mucosa with the cellophane membrane.

Viscosity.

During use, dilution is expected to occur in the vagina due to the volume of deposited semen, the presence of vaginal fluid, and the partial leakage of the gel from the vagina over time. To estimate the effect of such dilution, the viscosities of diluted inventive gel, as well as diluted commercially available vagina gels, were determined. Samples of vaginal formulations were weighed in 25 ml beakers. Deionized water (minimum resistance 16MW) was added to the gel samples to afford a 20 percent solution/suspension (w/v; 1 part gel to 4 parts water). Using a magnetic stirring bar, the samples were stirred for 30 minutes. The viscosity was determined at a temperature of 30.0±0.5 C. with a Brookfield DV–I+(LVT spindles) viscometer with small sample adapter (Spindle #18). The spindle speed was adjusted to provide the highest percentage torque value in the 10 to 100 percent range as recommended by the manufacturer.

The following results were obtained for the inventive gel and the various commercial vaginal gels.

TABLE XV

| Formulation | Viscosity (cps) |
|---|---|
| Inventive gel | 4332 |
| Aci-Jel ™ | 206 |
| Advantage S ™ | 16 |
| Conceptrol ™ | 42 |
| K-Y Jelly ™ | 41 |
| Replens ™ | 24 |

The inventive gel retained its viscosity upon dilution much better than the other gels. The viscosity of diluted inventive gel was 21, 271, 103, 103, and 180 times higher than Aci-Jel™, Advantage S™, Conceptrol™, K-Y Jelly™, and Replens™, respectively. Both the Replens™ and Advantage S™ formulations did not readily dissolve in water; indeed some components became attached to the surface of the container.

Spermicidal Activity.

In order to evaluate spermicidal activity, the inventive gel was diluted with saline (0.9 percent NaCl) to obtain samples having 200, 100, 50, 33, and 25 mg gel/ml saline. Five volumes of each diluted gel suspension were added to one volume of semen. The percentage of motile spermatozoa was determined 30 seconds after the addition of semen, under bright field microscopy, by a modification of the method of Sander and Cramer (Anderson et al., "Evaluation of Poly (Styrene-4-Sulfonate) as a Preventive Agent for Conception and Sexually Transmitted Diseases," *J. Androl.,* 2000 (in press); Sander et al., "A Practical Method for Testing the Spermicidal Action of Chemical Contraceptives," *Hum. Fertil.,* 1941; 6:134–7). Approximately 200 sperm were examined per sample. The following results were obtained.

TABLE XVI

| Undiluted Gel to Semen Ratio | pH | Motile Spermatozoa (%) |
|---|---|---|
| Semen only | 8.09 | 70 |
| 1:8 | 6.46 | 62 |

TABLE XVI-continued

| Undiluted Gel to Semen Ratio | pH | Motile Spermatozoa (%) |
|---|---|---|
| 1:6 | 6.04 | 54 |
| 1:4 | 5.54 | 33 |
| 1:2 | 4.56 | 0 |
| 1:1 | 3.97 | 0 |

The spermicidal activity of the inventive gel increased in a dose-dependent manner as the amount of gel in the mixture increased and the pH of the semen mixture decreased. Comparative studies (not shown) demonstrated that the inventive gel has much higher spermicidal activity compared to Aci-Jel™. For instance, a 1:2 ratio of undiluted inventive gel/semen had a pH of 4.56 and essentially complete sperm immobilization; the same dilution of Aci-Jel™ had a pH of 6.22 and essentially no effect on sperm motility under identical conditions.

Spermatozoa are generally inactivated at a pH 5.0 (Garg and Zaneveld, unpublished results; see also Mann, The Biochemistry of Seme," New York: Wiley, 1964.). Based on these results, a mixture of undiluted inventive gel and semen at a ratio of 1 to 3.4 should produce a pH of 5.0 and, thus, should be completely spermicidal. However, partial spermicidal activity can be seen at lower gel to semen ratios; for example, a 1:4 inventive gel to semen ratio produced about 33 percent inhibition of sperm motility. The $IC_{50}$ under the test conditions was calculated to be equivalent to an undiluted gel to semen ratio of 1 to 4.1.

Stability.

Plastic tubes containing the inventive gel were stored at 4 C., 27 C., and 40 C. Tubes were withdrawn at intervals of 1, 2, 3, and 6 months and the properties of the material stored at 27 C. and at 40 C. were compared to those maintained at 4 C. Comparisons were also performed between samples stored at 27 C. and 4 C. after storage for 24 months. The samples for analysis were obtained by making a longitudinal cut in the tube in a butterfly pattern (across top, across bottom, then down the middle connecting the top and bottom cuts opposite to the seam) after which the tube walls were carefully opened. The contents were observed for their appearance and color, and the tube walls for their condition and color changes. Test samples for analysis were obtained from the top, middle, and bottom regions of the tube. The pH of the three top, middle, and bottom regional samples were determined with a pH meter (Orion Model 230A with Orion Ross Sure-Flow Electrode). The buffering capacity of the samples was measured by mixing four 100 ml aliquotes (400 mL total) of 1N NaOH to 40 ml of a 5 percent aqueous solution of the sample and determining the pH. A Microbial Limit Test (for microbial contamination) and a Microbial Challenge Test (for preservative effectiveness; using *Staphylococcus aureus, Aspergillus niger, Candida albicans, Escherichia coli,* and *Pseudomonas aeruginosa*) were performed at selected time points for ambient and stress storage samples.

No changes were observed for general appearance, color, odor, consistency, homogeneity, pH, and buffering capacity for samples stored under accelerated stress conditions at 40 C. for up to 6 months or at ambient temperature for up to 24 months (the longest time periods measured) when compared to control samples stored at 4 C. In addition, the stored gels passed the microbial tests at all evaluation time points.

EXAMPLE 11

This example illustrates the trapping gels of the present invention formulated in tablet form which is designed to be inserted into the vagina. Tablets were prepared with the following formulation:

| Ingredient | Amount (%) |
|---|---|
| Xanthan gum | 2.0 |
| Alginic Acid | 2.65 |
| Sodium Alginate | 2.65 |
| Citric Acid | 2.0 |
| Lactic Acid | 2.0 |
| Tartaric Acid | 0.5 |
| Lactose | 63.0 |
| L-Hydroxypropyl Cellulose | 10.0 |
| D-Sorbitol | 5.0 |
| Sodium Starch Glycollate[a] | 5.0 |
| Benzoic Acid | 0.2 |
| Croscarmellose Sodium[b] | 3.0 |
| Magnesium Stearate | 1.0 |
| Talc | 1.0 |

[a]AC-Di-Sol ™ from Mendell, United Kingdom
[b]Explotab ™ from FMC, Belgium

All solid ingredients were accurately weighed in required quantities and passed through a number 85 sieve. An excipient blend was prepared by thoroughly mixing xanthan gum (about half of the total amount), alginic acid, sodium alginate, lactose, D-sorbitol, sodium starch glycollate, and L-hydroxypropyl cellulose on butter paper using a spatula; the excipient blend was then transferred to an air filled polyethylene bag and tumbled for 10 minutes to mix thoroughly. A binder solution of xanthan gum (the remaining amount), citric acid, lactic acid, benzoic acid, and tartaric acid dissolved in a small amount of distilled water was prepared. The amount of water in the binder solution was generally about 7 to 8 ml for a 30 g-formulation batch.

The binding solution was added to the excipient blend while mixing. Mixing was continued until all salts were incorporated into the formulation and the resulting wet mass could easily pass through a number 16 sieve. After passing the wet mass through a number 16 sieve, it was dried at 45° C. for 24 hours. The dried granules were then passed through a number 22 sieve. The resulting dried granules were mixed with the croscarmellose sodium, magnesium stearate, and talc in a polythene bag. The resulting mixture was then formed into tablets (about 1.2 g/tablet) using a single stroke tablet compression machine (Cadmach; Ahmedabad, Gujrat, India) using standard almond-shaped, concave punches.

As is well know in the art, other ingredients can be included in the tablets as desired and/or needed. Such optional ingredients include, for example, excipients such as xanthan gum, alginic acid, sodium alginate, citric acid, lactic acid, tartaric acid, benzoic acid, and the like; diluents such as lactose, dibasic calcium phosphate dihydrate, tribasic calcium phosphate, starch, sorbitol, microcrystalline cellulose, calcium carbonate, dextrose, mannitol, kaolin, and the like; disintegrants such as 1-hydroxypropyl cellulose, microcrystalline cellulose, sodium alginate, sodium starch glycollate, colloidal silicon dioxide, carboxymethyl cellulose sodium, carboxymethyl cellulose calcium, crospovidone, guar gum, methyl cellulose, croscarmellose sodium, and the like; humectants such as D-sorbitol, triacetin, polyhydric alcohols such as glycerol and propylene glycol; and lubricants/glidants such as magnesium stearate, talc, calcium stearate, stearic acid, castor soil, sodium lauryl sulphate, zinc stearate, glyceryl monostearate, boric acid, and the like.

When added to saline (one tablet in about 10 ml), the tablet swelled and disintegrated within about 3 to about 5 minutes. After about the first 2 minutes, approximately half the tablet had disintegrated; with continued disintegration, the viscosity of the dispersion increased. The initial pH of the dispersion was about 3.1. Buffering capacity was determined by titration with 0.97 N NaOH; the $pK_a$ value was about 2.96. Buffering capacity was sufficient to buffer and neutralize about 3 to about 7 ml of normal semen.

The bioadhesive strength of the tablets (one tablet added to about 10 ml saline) were measured using the horizontal bioadhesive test assembly described in Example 10 using cellophane membranes hydrated with stimulated vaginal fluids. Comparison with the following commercially available vaginal tablets was also made: (1) Candid-V6® (clotrimazole IP(100 mg); Glenmark Pharmaceuticals Ltd., Goa, India); (2) Betadine® (povidone-iodine IP 200 mg (available iodine 20 mg); Win-Medicare Ltd, New Delhi, India); (3) Infa-V® (Metronidazole IP (500 mg), Clotrimazole (100 mg), and Lactic acid Bacillus (150 million spores); Lark Laboratories (India) Ltd, New Delhi, India); (4) Candizole-To (Tinidazole IP (500 mg), Miconazole nitrate IP (200 mg), and Neomycin Sulphate IP equivalent to 20 mg of Neomycin; Foreva Women's Healthcare, Unichem Laboratories Ltd, Mumbai, India). The following results were obtained:

TABLE XVII

Bioadhesive strengths of vaginal tablet formulations using cellophane membrane

| Tablet Formulation | Bioadhesive Strength (dynes/cm$^2$; n = 5) |
| --- | --- |
| Inventive tablet | 944 ± 69 |
| Candid-V6 ® | 713 ± 70 |
| Betadine ® | 611 ± 74 |
| Infa-V ® | 643 ± 70 |
| Candizole-T ® | 529 ± 65 |

The bioadhesive strength of the inventive tablet was about 1.3, 1.5, 1.5, and 1.8 fold higher, respectively, than Candid-V6®, Betadine®, Infa-V®, and Candizole-T®.

The tablets of this invention can be inserted into the vagina to provide, in combination with vaginal or other fluids present in the vagina, the trapping gels of this invention. If desired, other ingredients such as, for example, colorants and flavorants, can be used in the vaginal tables to increase or improve the aesthetic appeal.

What is claimed is:

1. An antimicrobial and contraceptive composition that reduces the risk of transmission of, or infection by, a sexually transmitted disease through sexual activity involving a vagina of a female and a penis of a male, said composition comprising (1) about 1 to about 10 percent of a matrix-forming agent selected from the group consisting of alginic acid, chitosan, gellan gum, and poloxamer, (2) about 1 to about 10 percent of a bio-adhesive agent selected from the group consisting of xanthan gum, hydroxypropyl cellulose, hydroxypropyl methyl cellulose, sodium carboxymethyl cellulose, chitosan, polycarbophil, and a crosslinked polyacrylic acid, (3) about 1 to about 10 percent of a buffering agent selected from the group consisting of lactic acid, citric acid, potassium acid tartrate, benzoic acid, alginic acid, sorbic acid, fumaric acid, ascorbic acid, stearic acid, oleic acid, tartaric acid, edetic acid, and malic acid, and (4) water; wherein the composition is suitable for application within the vagina; wherein the composition forms a semisolid matrix on contact with semen; wherein the composition causes hardening of cervical mucus; wherein the composition forms a bio-adhesive layer over vaginal surfaces; wherein the composition maintains an acidic vaginal pH of less than about 5 in the presence of semen ejaculated from the male; wherein the composition is hypertonic: and wherein the composition is antimicrobial and contraceptive without addition of antimicrobial or contraceptive agents.

2. The composition as defined in claim 1, wherein the composition further comprises a humectant and a preservative.

3. The composition as defined in claim 1, wherein the composition further comprises an antimicrobial or contraceptive agent.

4. The composition as defined in claim 2, wherein the composition further comprises an antimicrobial or contraceptive agent.

5. The composition as defined in claim 1, wherein the composition maintains the acidic vaginal pH in the range of about 3.5 to about 4.5; and wherein the composition does not significantly impair the natural microbiological balance within the vagina.

6. The composition as defined in claim 2, wherein the composition contains about 3 to about 5 percent of the matrix-forming agent, about 2.5 to about 6 percent of the bio-adhesive agent, about 1 to about 7 percent of the buffering agent, about 6 to about 10 percent of the humectant, and about 0.1 to about 1 percent of the preservative; wherein the composition maintains the acidic vaginal pH in the range of about 3.5 to about 4.5; and wherein the composition does not significantly impair the natural microbiological balance within the vagina.

7. The composition as defined in claim 4, wherein the composition contains about 3 to about 5 percent of the matrix-forming agent, about 2.5 to about 6 percent of the bio-adhesive agent, about 1 to about 7 percent of the buffering agent, about 6 to about 10 percent of the humectant, about 0.1 to about 1 percent of the preservative, and about 0.2 to about 5 percent of the antimicrobial or contraceptive agent; wherein the composition maintains the acidic vaginal pH in the range of about 3.5 to about 4.5; and wherein the composition does not significantly impair the natural microbiological balance within the vagina.

8. The composition as defined in claim 2, wherein the humectant is selected from the group consisting of glycerol, polyethylene glycols, propylene glycols, sorbitol, and triacetin; and wherein the preservative is selected from the group consisting of benzoic acid, sodium benzoate, methylparaben, ethylparaben, butylparaben, propylparaben, benyalkonium chloride, phenylmercuric nitrate, and chlorhexidine.

9. The composition as defined in claim 4, wherein the humectant is selected from the group consisting of glycerol, polyethylene glycols, propylene glycols, sorbitol, and triacetin; wherein the preservative is selected from the group consisting of benzoic acid, sodium benzoate, methylparaben, ethylparaben, butylparaben, propylparaben, benyalkonium chloride, phenylmercuric nitrate, and chlorhexidine; and wherein the antimicrobial or contraceptive agent is selected from the group consisting of nonoxynol-9, octoxynol-9, benzalkonium chloride, phosphorylated hesperidins, sulfonated hesperidins, polystyrene sulfonates, substituted benzenesulfonic acid formaldehyde co-polymers, $H_2SO_4$-modified mandelic acids, povidone iodine, itraconazole, ketoconazole, metronidazole, clotrimazole, fluconazole, teraconazole, miconazole, tinidazole, iconazole, chloramphenicol, nystatin, and cyclopiroxolamine.

10. The composition as defined in claim 4, wherein the matrix-forming agent is alginic acid; wherein the bioadhesive agent is xanthan gum or hydroxypropyl cellulose; wherein the buffering agent is selected from the group consisting of lactic acid, citric acid, and potassium acid tartrate; wherein the humectant is selected from the group consisting of glycerol, polyethylene glycols, propylene glycols, sorbitol, and triacetin; wherein the preservative is selected from the group consisting of benzoic acid and sodium benzoate; and wherein the antimicrobial or contraceptive agent is selected from the group consisting of nonoxynol-9, octoxynol-9, benzalkonium chloride, phosphorylated hesperidins, sulfonated hesperidins, polystyrene sulfonates, substituted benzenesulfonic acid formaldehyde co-polymers, and $H_2SO_4$-modified mandelic acids.

11. A method of reducing the risk of transmission and infection by a sexually transmitted disease through sexual activity involving a vagina of a female and a penis of a male, said method comprising administering an effective amount of an antimicrobial and contraceptive composition within the vagina prior to, or shortly after, sexual activity; wherein the composition comprises (1) about 1 to about 10 percent of a matrix-forming agent selected from the group consisting of alginic acid, chitosan, gellan gum, and poloxamer, (2) about 1 to about 10 percent of a bio-adhesive agent selected from the group consisting of xanthan gum, hydroxypropyl cellulose, hydroxypropyl methyl cellulose, sodium carboxymethyl cellulose, chitosan, polycarbophil, and a crosslinked polyacrylic acid, (3) about 1 to about 10 percent of a buffering agent selected from the group consisting of lactic acid, citric acid, potassium acid tartrate, benzoic acid, alginic acid, sorbic acid, fumaric acid, ascorbic acid, stearic acid, oleic acid, tartaric acid, edetic acid, and malic acid, and (4) water; wherein the composition is suitable for application within the vagina; wherein the composition forms a semisolid matrix on contact with semen; wherein the composition causes the hardening of cervical mucus; wherein the composition forms a bio-adhesive layer over vaginal surfaces; wherein the composition maintains an acidic vaginal pH of less than about 5 in the presence of semen ejaculated from the male; wherein the composition is hypertonic; and wherein the composition is antimicrobial and contraceptive without addition of antimicrobial or contraceptive agents.

12. The method as defined in claim 11, wherein the composition further comprises a humectant and a preservative.

13. The method as defined in claim 11, wherein the composition further comprises an antimicrobial or contraceptive agent.

14. The method as defined in claim 12, wherein the composition further comprises an antimicrobial or contraceptive agent.

15. The method as defined in claim 11, wherein the composition maintains the acidic vaginal pH in the range of about 3.5 to about 4.5; and wherein the composition does not significantly impair the natural microbiological balance within the vagina.

16. The method as defined in claim 12, wherein the composition contains about 3 to about 5 percent of the matrix-forming agent, about 2.5 to about 6 percent of the bio-adhesive agent, about 1 to about 7 percent of the buffering agent, about 6 to about 10 percent of the humectant, and about 0.1 to about 1 percent of the preservative; wherein the composition maintains the acidic vaginal pH in the range of about 3.5 to about 4.5; and wherein the composition does not significantly impair the natural microbiological balance within the vagina.

17. The method as defined in claim 14, wherein the composition contains about 3 to about 5 percent of the matrix-forming agent, about 2.5 to about 6 percent of the bio-adhesive agent, about 1 to about 7 percent of the buffering agent, about 6 to about 10 percent of the humectant, about 0.1 to about 1 percent of the preservative, and about 0.2 to about 5 percent of the antimicrobial or contraceptive agent; wherein the composition maintains the acidic vaginal pH in the range of about 3.5 to about 4.5; and wherein the composition does not significantly impair the natural microbiological balance within the vagina.

18. The method as defined in claim 12, wherein the humectant is selected from the group consisting of glycerol, polyethylene glycols, propylene glycols, sorbitol, and triacetin; and wherein the preservative is selected from the group consisting of benzoic acid, sodium benzoate, methylparaben, ethylparaben, butylparaben, propylparaben, benyalkonium chloride, phenylmercuric nitrate, and chlorhexidine.

19. The method as defined in claim 14, wherein the humectant is selected from the group consisting of glycerol, polyethylene glycols, propylene glycols, sorbitol, and triacetin; wherein the preservative is selected from the group consisting of benzoic acid, sodium benzoate, methylparaben, ethylparaben, butylparaben, propylparaben, benyalkonium chloride, phenylmercuric nitrate, and chlorhexidine; and wherein the antimicrobial or contraceptive agent is selected from the group consisting of nonoxynol-9, octoxynol-9, benzalkonium chloride, phosphorylated hesperidins, sulfonated hesperidins, polystyrene sulfonates, substituted benzenesulfonic acid formaldehyde co-polymers, $H_2SO_4$-modified mandelic acids, itraconazole, ketoconazole, and metronidazole.

20. The method as defined in claim 12, wherein the matrix-forming agent is alginic acid; wherein the bio-adhesive agent is xanthan gum or hydroxypropyl cellulose; wherein the buffering agent is selected from the group consisting of lactic acid, citric acid, and potassium acid tartrate; wherein the humectant is selected from the group consisting of glycerol, polyethylene glycols, propylene glycols, sorbitol, and triacetin; wherein the preservative is selected from the group consisting of benzoic acid and sodium benzoate; and wherein the antimicrobial or contraceptive agent is selected from the group consisting of nonoxynol-9, octoxynol-9, benzalkonium chloride, phosphorylated hesperidins, sulfonated hesperidins, polystyrene sulfonates, substituted benzenesulfonic acid formaldehyde co-polymers, and $H_2SO_4$-modified mandelic acids.

21. An antimicrobial and contraceptive composition for reducing the risk of transmission and infection by a sexually transmitted disease through sexual activity, said composition comprising (1) about 1 to about 10 percent of a matrix-forming agent selected from the group consisting of alginic acid, chitosan, gellan gum, and poloxamer, (2) about 1 to about 10 percent of a bio-adhesive agent selected from the group consisting of xanthan gum, hydroxypropyl cellulose, hydroxypropyl methyl cellulose, sodium carboxymethyl cellulose, chitosan, polycarbophil, and a crosslinked polyacrylic acid, (3) about 1 to about 10 percent of a buffering agent selected from the group consisting of lactic acid, citric acid, potassium acid tartrate, benzoic acid, alginic acid, sorbic acid, fumaric acid, ascorbic acid, stearic acid, oleic acid, tartaric acid, edetic acid, and malic acid, (4) 0 to about 2 percent of a humectant, (5) 0 to about 2 percent of a preservative, (6) 0 to about 10 percent of an antimicrobial or contraceptive agent, and (7) water; wherein the composition is suitable for application within a vagina; wherein the composition forms a semisolid matrix on contact with semen ejaculated from a male into the vagina; wherein the composition causes hardening of cervical mucus of the vagina; wherein the composition forms a bio-adhesive layer over vaginal surfaces; wherein the composition maintains an acidic vaginal pH of less than about 5 in the presence of semen ejaculated from the male; wherein the composition is hypertonic; and wherein the composition is antimicrobial and contraceptive without addition of antimicrobial or contraceptive agents.

22. The composition as defined in claim 21, wherein the composition contains about 3 to about 5 percent of the matrix-forming agent, about 2.5 to about 6 percent of the bio-adhesive agent, about 1 to about 7 percent of the buffering agent, about 6 to about 10 percent of the humectant, and about 0.1 to about 1 percent of the preservative; wherein the composition maintains the acidic vaginal pH in the range of about 3.5 to about 4.5; and wherein the composition does not significantly impair the natural microbiological balance within the vagina.

23. The composition as defined in claim 21, wherein the matrix-forming agent is alginic acid; wherein the bio-adhesive agent is xanthan gum or hydroxypropyl cellulose; wherein the buffering agent is selected from the group consisting of lactic acid, citric acid, and potassium acid tartrate; wherein the humectant, if present, is selected from the group consisting of glycerol, polyethylene glycols, propylene glycols, sorbitol, and triacetin; wherein the preservative, if present, is selected from the group consisting of benzoic acid and sodium benzoate; and wherein the antimicrobial or contraceptive agent, if present, is selected from the group consisting of nonoxynol-9, octoxynol-9, benzalkonium chloride, phosphorylated hesperidins, sulfonated hesperidins, polystyrene sulfonates, substituted benzenesulfonic acid formaldehyde co-polymers, and $H_2SO_4$-modified mandelic acids.

24. The composition as defined in claim 22, wherein the matrix-forming agent is alginic acid; wherein the bio-adhesive agent is xanthan gum or hydroxypropyl cellulose; wherein the buffering agent is selected from the group consisting of lactic acid, citric acid, and potassium acid tartrate; wherein the humectant is selected from the group consisting of glycerol, polyethylene glycols, propylene glycols, sorbitol, and triacetin; wherein the preservative is selected from the group consisting of benzoic acid and sodium benzoate; and wherein the antimicrobial or contraceptive agent is selected from the group consisting of nonoxynol-9, octoxynol-9, benzalkonium chloride, phosphorylated hesperidins, sulfonated hesperidins, polystyrene sulfonates, substituted benzenesulfonic acid formaldehyde co-polymers, and $H_2SO_4$-modified mandelic acids.

25. A solid composition that reduces the risk of transmission of, or infection by, a sexually transmitted disease through sexual activity involving a vagina of a female and a penis of a male, said solid composition comprising (1) a matrix-forming agent selected from the group consisting of alginic acid, chitosan, gellan gum, and poloxamer, (2) a bio-adhesive agent selected from the group consisting of xanthan gum, hydroxypropyl cellulose, hydroxypropyl methyl cellulose, sodium carboxymethyl cellulose, chitosan, polycarbophil, and a crosslinked polyacrylic acid, and (3) a buffering agent selected from the group consisting of lactic acid, citric acid, potassium acid tartrate, benzoic acid, alginic acid, sorbic acid, fumaric acid, ascorbic acid, stearic acid, oleic acid, tartaric acid, edetic acid, and malic acid; wherein the solid composition is suitable for application within the vagina; wherein the solid composition is readily dispersable in aqueous based medium either outside or inside the vagina to form a dispersed composition; wherein the solid composition contains sufficient matrix-forming agent, bio-adhesive agent, and buffering agent to provide the dispersed composition containing about 1 to about 10 percent of the matrix-forming agent, about 1 to about 10 percent of the bio-adhesive agent, and about 1 to about 10 percent of the buffering agent within the vagina; wherein the dispersed composition forms a semisolid matrix on contact with semen; wherein the dispersed composition causes hardening of cervical mucus; wherein the dispersed composition forms a bio-adhesive layer over vaginal surfaces; wherein the dispersed composition maintains an acidic vaginal pH of less than about 5 in the presence of semen ejaculated from the male; wherein the dispersed composition is hypertonic; and wherein the dispersed composition is antimicrobial and contraceptive without addition of antimicrobial or contraceptive agents.

26. The solid composition as defined in claim 25, wherein the solid composition further comprises a humectant and a preservative.

27. The solid composition as defined in claim 25, wherein the solid composition further comprises an antimicrobial or contraceptive agent.

28. The solid composition as defined in claim 26, wherein the solid composition further comprises an antimicrobial or contraceptive agent.

29. The solid composition as defined in claim 25, wherein the dispersed composition maintains the acidic vaginal pH in the range of about 3.5 to about 4.5; and wherein the dispersed composition does not significantly impair the natural microbiological balance within the vagina.

30. The solid composition as defined in claim 26, wherein the solid composition contains sufficient matrix-forming agent, bio-adhesive agent, and buffering agent to provide the dispersed composition containing about 3 to about 5 percent of the matrix-forming agent, about 2.5 to about 6 percent of the bio-adhesive agent, about 1 to about 7 percent of the buffering agent, about 6 to about 10 percent of the humectant, and about 0.1 to about 1 percent of the preservative within the vagina; wherein the dispersed composition maintains the acidic vaginal pH in the range of about 3.5 to about 4.5; and wherein the dispersed composition does not significantly impair the natural microbiological balance within the vagina.

31. The solid composition as defined in claim 28, wherein the solid composition contains sufficient matrix-forming agent, bio-adhesive agent, and buffering agent to provide the dispersed composition containing about 3 to about 5 percent of the matrix-forming agent, about 2.5 to about 6 percent of the bio-adhesive agent, about 1 to about 7 percent of the buffering agent, about 6 to about 10 percent of the humectant, about 0.1 to about 1 percent of the preservative, and about 0.2 to about 5 percent of the antimicrobial or contraceptive agent within the vagina; wherein the dispersed composition maintains the acidic vaginal pH in the range of about 3.5 to about 4.5; and wherein the dispersed composition does not significantly impair the natural microbiological balance within the vagina.

32. The composition as defined in claim 26, wherein the humectant is selected from the group consisting of glycerol, polyethylene glycols, propylene glycols, sorbitol, and triacetin; and wherein the preservative is selected from the group consisting of benzoic acid, sodium benzoate, methylparaben, ethylparaben, butylparaben, propylparaben, benyalkonium chloride, phenylmercuric nitrate, and chlorhexidine.

33. The solid composition as defined in claim 28, wherein the humectant is selected from the group consisting of glycerol, polyethylene glycols, propylene glycols, sorbitol, and triacetin; wherein the preservative is selected from the group consisting of benzoic acid, sodium benzoate, methylparaben, ethylparaben, butylparaben, propylparaben, benyalkonium chloride, phenylmercuric nitrate, and chlorhexidine; and wherein the antimicrobial or contraceptive agent is selected from the group consisting of nonoxynol-9, octoxynol-9, benzalkonium chloride, phosphorylated hesperidins, sulfonated hesperidins, polystyrene sulfonates, substituted benzenesulfonic acid formaldehyde co-polymers, $H_2SO_4$-modified mandelic acids, povidone iodine, itraconazole, ketoconazole, metronidazole, clotrimazole, fluconazole, teraconazole, miconazole, tinidazole, iconazole, chloramphenicol, nystatin, and cyclopiroxolamine.

34. The solid composition as defined in claim 28, wherein the matrix-forming agent is alginic acid; wherein the bioadhesive agent is xanthan gum or hydroxypropyl cellulose; wherein the buffering agent is selected from the group consisting of lactic acid, citric acid, and potassium acid tartrate; wherein the humectant is selected from the group consisting of glycerol, polyethylene glycols, propylene glycols, sorbitol, and triacetin; wherein the preservative is selected from the group consisting of benzoic acid and sodium benzoate; and wherein the antimicrobial or contraceptive agent is selected from the group consisting of nonoxynol-9, octoxynol-9, benzalkonium chloride, phosphorylated hesperidins, sulfonated hesperidins, polystyrene sulfonates, substituted benzenesulfonic acid formaldehyde co-polymers, and $H_2SO_4$-modified mandelic acids.

35. The solid composition as defined in claim 25, wherein the solid composition is in the form of a tablet which can be inserted into the vagina.

36. The solid composition as defined in claim 31, wherein the solid composition is in the form of a tablet which can be inserted into the vagina.

* * * * *